United States Patent

Rheinheimer et al.

[11] Patent Number: 5,569,640
[45] Date of Patent: Oct. 29, 1996

[54] SUBSTITUTED 1,3-BENZADIOXANE-4-ONES AND 1,3-BENZATHIOXANE-4-ONES, THEIR PREPARATION AND THEIR CONVERSION TO CROP PROTECTION AGENTS

[76] Inventors: Joachim Rheinheimer, Merziger Str. 24, 67063 Ludwigshafen; Uwe J. Vogelbacher, Niedererdstr. 56, 67071 Ludwigshafen; Ernst Baumann, Falkenstr. 6a, 67373 Dudenhofen; Hartmann König, Albert-Einstein-Allee 16; Matthias Gerber, Brandenburger Str. 24, both of 67117 Limburgerhof; Karl-Otto Westphalen, Mausbergweg 58, 67346 Speyer; Helmut Walter, Grünstadter Strasse 82, 67283 Obrigheim, all of Germany

[21] Appl. No.: 332,083

[22] Filed: Nov. 1, 1994

[30] Foreign Application Priority Data

Nov. 2, 1993 [DE] Germany .................. 43 37 321.6

[51] Int. Cl.⁶ .................. A01N 43/32; C07D 319/08; C07D 339/08; C07D 327/06
[52] U.S. Cl. .................. 504/288; 504/293; 549/16; 549/330; 549/365
[58] Field of Search .................. 504/288, 293; 549/16, 330, 365

[56] References Cited

U.S. PATENT DOCUMENTS

| 5,085,686 | 2/1992 | Vogelbacher | 71/92 |
| 5,362,876 | 11/1994 | Eicken et al. | 544/278 |

FOREIGN PATENT DOCUMENTS

| 249708 | 4/1987 | European Pat. Off. . |
| 287079 | 4/1988 | European Pat. Off. . |
| 0272223 | 6/1988 | European Pat. Off. . |
| 278072 | 8/1988 | European Pat. Off. . |
| 315889 | 5/1989 | European Pat. Off. . |
| 346789 | 6/1989 | European Pat. Off. . |
| 490060 | 6/1992 | European Pat. Off. . |
| 0527378 | 7/1993 | European Pat. Off. . |
| 93/03017 | 2/1993 | WIPO . |

OTHER PUBLICATIONS

Chem. Abst., vol. 91 (23), 1979, A.N. 193238u.
Chem. Abst., vol. 120, No. 22, May 30, 1994, Abst. No. 273469c, Hadfield et al., p. 154, 1994.
Chem. Abst., vol. 115, No. 12, Sep. 23, 1991, Abst. No. 119912g, Hundewadt et al., p. 345, 1991.
Chem. Abst., vol. 97, No. 15, Oct. 11, 1982, Abst. No. 127582z, Al–Rawi et al., p. 722, 1982.
CA91:193237t, 1979.
Barbary et al. Tetrahedron 36, pp. 3309–3315, 1990.
McCollum et al., Inog. Chem. 33, pp. 924–933, 1994
Hiroyuki et al. Chem. Pharm. Bull., 27(2), pp. 522–527 1979.
Yuzuru et al, The Chemical Society of Japan, 54; 1781–1786 1981.

Primary Examiner—Yogendra N. Gupta

[57] ABSTRACT

Cyclic acetals of the formula I

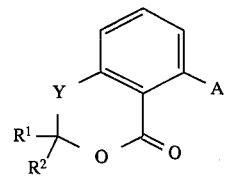

where the substituents have the following meanings:

$R^1$ and $R^2$ are hydrogen, unsubstituted or substituted alkyl or phenyl; additionally $R^1$ and $R^2$ together are an unsubstituted or substituted $C_2$–$C_6$-alkylene chain;

Y is oxygen or sulfur;

A has the meaning as given in claim 1;

a process for preparing the acetals I and their use for the production of crop protection compositions are described.

1 Claim, No Drawings

SUBSTITUTED 1,3-BENZADIOXANE-4-ONES AND 1,3-BENZATHIOXANE-4-ONES, THEIR PREPARATION AND THEIR CONVERSION TO CROP PROTECTION AGENTS

The present invention relates to cyclic acetals of the formula I

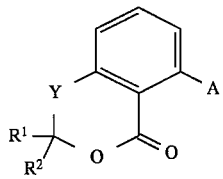

where the substituents have the following meanings:

$R^1$ and $R^2$ are hydrogen;
$C_1$–$C_4$-alkyl, this radical in each case being able to carry one to five halogen atoms and/or one to two $C_1$–$C_4$-alkoxy groups;
phenyl, this radical in each case being able to carry one to five halogen atoms and/or one to two of the following groups:
$C_1$–$C_4$-alkyl, $C_1$–$C_4$-alkoxy, $C_1$–$C_4$-haloalkyl or nitro;
in addition the two radicals together can be a $C_2$–$C_6$-alkylene chain which can be substituted by one to five halogen atoms and/or $C_1$–$C_4$-alkyl radicals;

Y is oxygen or sulfur;

A is a radical $A^1$ to $A^6$;

$A^1$ is hydroxyl;

$A^2$ is a halogen atom, $C_1$–$C_4$-haloalkylsulfonyloxy, $C_1$–$C_4$-alkylsulfonyloxy or fluorosulfonyloxy;

$A^3$ is cyano, nitro or formyl;

$A^4$ is a phenyl ring or a 5- or 6-membered saturated or unsaturated heterocycle having up to four heteroatoms from the group consisting of nitrogen, sulfur and oxygen in the ring, each of which can be substituted by up to five radicals $R^{31}$ to $R^{35}$;
naphthyl or a benzo-fused 5- or 6-membered heteroaromatic having 1 to 3 heteroatoms from the group consisting of nitrogen, sulfur and oxygen in the ring, which can be substituted by up to five radicals $R^{31}$ to $R^{35}$;

$A^5$ is a $C_2$–$C_6$-alkenyl, $C_3$–$C_8$-cycloalkenyl, $C_5$–$C_8$-cycloalkadienyl or $C_2$–$C_6$-alkynyl group, each of which can carry up to seven substituents $R^{31}$ to $R^{37}$;

$A^6$ is a $C_1$–$C_8$-alkyl or $C_3$–$C_8$-cycloalkyl group, each of which can carry up to seven substituents $R^{31}$ to $R^{37}$;

$R^{31}$, $R^{32}$, $R^{33}$, $R^{34}$, $R^{35}$, $R^{36}$ and $R^{37}$ are
a) a $C_3$–$C_4$-cycloalkyl group which can carry one to three $C_1$–$C_4$-alkyl radicals;
b) a $C_1$–$C_8$-alkyl group which can carry one to five halogen atoms and/or one of the following radicals: $C_1$–$C_4$-alkoxy, $C_1$–$C_4$-haloalkoxy, $C_1$–$C_4$-alkylthio, cyano, $C_3$–$C_8$-cycloalkyl or di-$C_1$–$C_4$-alkylamino;
c) a $C_1$–$C_8$-alkoxy group or a $C_3$–$C_5$-cycloalkoxy group, each of which can carry one to five halogen atoms and/or one of the following radicals:
$C_1$–$C_4$-alkoxy, $C_1$–$C_4$-haloalkoxy, $C_1$–$C_4$-alkylthio, $C_3$–$C_8$-cycloalkyl or di-$C_1$–$C_4$-alkylamino;
d) a $C_1$–$C_4$-alkylthio group which can carry one to five halogen atoms and/or one of the following radicals:
$C_1$–$C_4$-alkoxy, $C_1$–$C_4$-haloalkoxy, $C_1$–$C_4$-alkylthio, $C_3$–$C_8$-cycloalkyl or di-$C_1$–$C_4$-alkylamino;
e) a di-$C_1$–$C_4$-alkylamino or a di-$C_1$–$C_4$-alkylaminoxy group, a $C_5$–$C_8$-cycloalkaniminoxy group or a $C_1$–$C_{10}$-alkaniminoxy group;
f) a $C_2$–$C_6$-alkenyl or a $C_2$–$C_6$-alkynyl group, which can carry one to five halogen atoms and/or one of the following radicals:
$C_1$–$C_4$alkoxy, $C_1$–$C_4$-haloalkoxy or $C_1$–$C_4$-alkylthio;
g) hydrogen;
h) nitro, halogen, cyano or tri-$C_1$–$C_4$-alkylsilyl;
with the proviso that A is not a hydroxyl group if $R^1$ and $R^2$ are both hydrogen or if $R^1$ is hydrogen and $R^2$ is phenyl.

The abovementioned compounds are used in particular as intermediates for the preparation of crop protection agents, eg. of substituted salicylic acid derivatives which, according to the prior art (eg. DE-A 39 19 435, EP-A 346 789, EP-A 490 060, WO 93/03017, EP-A 249 708, 287 072, 287 079 and 315 889) have good herbicidal and/or bioregulatory action. However, they also show a good herbicidal action themselves.

The preparation of 1,3-benzodioxoles and benzodioxane derivatives is described in Chemical Abstracts 91 (23): 193238u (L. Bonsignore et al., Rend. Semin. Fac. Sci. Univ. Cagliari, Vol. 48, (1978) pp. 275–283).

It is an object of the present invention to facilitate access to various substituted salicylic acid derivatives, eg. the compounds described in the above publications, and to make available an advantageous process for preparing these compounds.

We have now found that this object can be achieved by the cyclic acetals I mentioned at the outset. We have furthermore found an advantageous method for reaction of the acetals I to give the biologically active compounds. The invention further relates to chemically discrete processes for preparing the acetals I, herbicidal compositions containing the compounds I and their use for controlling undesired plant growth.

In the description, the substituents mentioned below preferably have the following meanings:

$C_1$–$C_4$-alkyl: methyl, ethyl, 1-propyl, 2-propyl, 2-methyl-2-propyl, 2-methyl-1-propyl, 1-butyl, 2-butyl;

$C_1$–$C_8$-alkyl: $C_1$–$C_4$-alkyl and also pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl;

$C_1$–$C_2$-haloalkyl: fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$–$C_2$-haloalkoxy: difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro- 1,1,2-trifluoroethoxy and pentafluoroethoxy;

$C_1$–$C_4$-alkoxy: methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy;

$C_1$–$C_4$-alkylthio: methylthio, ethylthio, propylthio, 1-methylethylthio, butylthio, 1-methylpropylthio, 2-methylpropylthio, 1,1-dimethylethylthio, in particular methylthio and ethylthio;

$C_3$–$C_6$-alkenyl: 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 4-methyl-4-pentenyl, 2-methyl-4-pentenyl, 3-methyl-4-pentenyl, 4-methyl-4-pentenyl, 1,1-dimethyl-2-butenyl, 1,1-dimethyl- 3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1 -methyl-2-propenyl and 1-ethyl-2-methyl-2-propenyl;

$C_3$–$C_6$-alkynyl: 2-propynyl, 2-butynyl, 3-butynyl, 1-methyl- 2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

halogen: chlorine, bromine, iodine, fluorine;

$C_3$–$C_8$-cycloalkenyl: cyclopropenyl, cyclobutenyl, cyclopentenyl, cyclohexenyl, cycloheptenyl, cyclooctenyl, particularly preferably cyclopentenyl, cycloheptenyl and cyclooctenyl;

$C_5$–$C_8$-cycloalkadienyl: cyclopentadienyl, 1,3-cyclohexadienyl, 1,4-cyclohexadienyl, 1,3-cycloheptadienyl, 1,4-cycloheptadienyl, 1,3-cyclooctadienyl, 1,4-cyclooctadienyl, 1,5-cyclooctadienyl;

$C_3$–$C_8$-cycloalkyl: cyclopropyl, cyclobutyl, cyclopentyl, cyclohexyl, cycloheptyl and cyclooctyl, particularly preferably cyclopropyl, cyclopentyl and cyclohexyl;

di-$C_1$–$C_4$-alkylaminoxy: dimethylaminoxy, N-methyl-N-ethylaminoxy, diethylaminoxy, N-methyl-N-propylaminoxy, N-ethyl-N-propylaminoxy, dipropylaminoxy, diisopropylaminoxy, N-isopropyl-N-methylaminoxy, N-ethyl-N-isopropylaminoxy, N-isopropyl-N-propylaminoxy, dibutylaminoxy, di-2-methylpropylaminoxy, di-1-methylpropylaminoxy, N-butyl-N-methylaminoxy and isomers, N-butyl-N-ethylaminoxy and isomers, N-butyl-N-propylaminoxy and isomers;

$C_1$–$C_{10}$-alkaniminoxy: methaniminoxy, ethaniminoxy, 1-propaniminoxy, 2-propaniminoxy, 1-butaniminoxy, 2-butaniminoxy, 2-methylpropan-1-iminoxy, 1-pentaniminoxy, 2-pentaniminoxy, 3-pentaniminoxy, 3-methylbutan-2-iminoxy, 3-methylbutan-1-iminoxy, 2-methylbutan-1-iminoxy, 2,2-dimethylpropan-1-iminoxy, hexaniminoxy and isomers, heptaniminoxy and isomers, octaniminoxy and isomers, nonaniminoxy and isomers, decaniminoxy and isomers; 2-propaniminoxy, 2-butaniminoxy, 2-pentaniminoxy, 3-pentaniminoxy, 2-hexaniminoxy, 3-hexaniminoxy and 2, 2-dimethylpropan- 1-iminoxy are very particularly preferred;

$C_5$–$C_8$-cycloalkaniminoxy: cyclopentaniminoxy, cyclohexaniminoxy, cycloheptaniminoxy, cyclooctaniminoxy;

di-$C_1$–$C_4$-alkylamino: dimethylamino, N-methyl-N-ethylamino, diethylamino, N-methyl-N-propylamino, N-ethyl-N-propylamino, dipropylamino, diisopropylamino, N-isopropyl-N-methylamino, N-ethyl-N-isopropylamino, N-isopropyl-N-propylamino, dibutylamino, di-2-methylpropylamino, di-1-methylpropylamino, N-butyl-N-methylamino and isomers, N-butyl-N-ethylamino and isomers, N-butyl-N-propylamino and isomers.

With respect to the intended use of the final products (eg. salicylic acid derivatives IV), compounds of the formula I are preferred as intermediates in which the substituents have the following meanings:

$R^1$ and $R^2$ are hydrogen;

$C_1$–$C_4$-alkyl, this radical in each case being able to carry one to five halogen atoms and/or one to two $C_1$–$C_4$-alkoxy groups, methyl and ethyl are very particularly preferred;

phenyl, this radical in each case being able to carry one to five halogen atoms and/or one to two of the following groups: $C_1$–$C_4$-alkyl, $C_1$–$C_4$-alkoxy, $C_1$–$C_4$-haloalkyl, preferably $C_1$–$C_2$-haloalkyl or nitro; phenyl is very particularly preferred;

in addition the two radicals together can be a $C_2$–$C_6$-alkylene chain, such as a 1,2-ethylene, 1,3-propylene, 1,4-butylene, 1,5-pentylene or 1,6-hexylene group, which can be substituted by one to five halogen atoms and/or $C_1$–$C_4$-alkyl radicals; the 1,4-butylene and 1,5-pentylene groups are very particularly preferred;

A is a radical $A^1$ to $A^6$;

$A^1$ is hydroxyl;

$A^2$ is a halogen atom, $C_1$–$C_4$-haloalkylsulfonyloxy, $C_1$–$C_4$-alkylsulfonyloxy or fluorosulfonyloxy;

$A^3$ is cyano, nitro or formyl;

$A^4$ is a phenyl-ring or a 5- or 6-membered saturated or unsaturated heterocycle having one to four heteroatoms from the group consisting of nitrogen, sulfur and oxygen in the ring, such as phenyl, pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,4,5-tetrazin-3-yl, tetrahydrothiopyran-2-yl, tetrahydrothiopyran-3-yl, tetrahydrothiopyran- 4-yl, tetrahydropyran-2-yl, tetrahydropyran-3-yl, tetrahydropyran-4-yl, dihydropyranyl, dihydrothiopyranyl, piperidin-2-yl, piperidin-3-yl, piperidin-4-yl, morpholin-2-yl, morpholin-3-yl, furan-2-yl, furan-3-yl, 2-thienyl, 3-thienyl, tetrahydrofuran-2-yl, tetrahydrofuran-3-yl, 2,3-dihydrofuran-3-yl, 2,3-dihydrofuran-2-yl, 2,3-dihydrofuran-4-yl, 2,3-dihydrofuran- 5-yl, 3,4-dihydrofuran-2-yl, 3,4-dihydrofuran-3-yl, 2,3-dihydrothien-3-yl, 2,3-dihydrothien-2-yl, 2,3-dihydrothien- 4-yl, 2,3-dihydrothien-5-yl, 3,4-dihydrothien-2-yl, 3,4-dihydrothien-3-yl, tetrahydrothien-2-yl, tetrahydrothien- 3-yl, 2-pyrrolyl, 3-pyrrolyl, 2-pyrrolidinyl, 3-pyrrolidinyl, imidazol-2-yl, imidazol-4-yl, imidazol-5-yl, pyrazol-3-yl, pyrazol-4-yl, pyrazol-5-yl, 1,2,3-triazol-4-yl, 1,2,3-triazol-5-yl, 1,2,4-triazol-3-yl, 1,2,4-triazol-5-yl, tetrazol-5-yl, 1,2,3-thiadiazol-4-yl, 1,2,3-thiadiazol-5-yl, 1,2,5-thiadiazol-3-yl, 1,3,4-thiadiazol-2-yl, 1,2,4-thiadiazol-3-yl, 1,2,4-thiadiazol-5-yl, 1,2,3-oxadiazol-4-yl, 1,2,3-oxadiazol-5-yl, 1,2,5-oxadiazol-3-yl, 1,3,4-oxadiazol-2-yl, 1,2,4-oxadiazol-3-yl, 1,2,4-oxadiazol-5-yl, 1,3-dioxolan-2-yl, 1,3-dioxolan-4-yl, 1,3-dithiolan-2-yl, 1,3-dithiolan-4-yl, oxazol-2-yl, oxazol-4-yl, oxazol-5-yl, oxazolin-2-yl, oxazolin-4-yl, oxazolin-5-yl, isoxazol-2-yl, isoxazol-4-yl, isoxazol-5-yl, isoxazolin-2-yl, isoxazolin-4-yl, isoxazolin-5-yl, thiazol-2-yl, thiazol-4-yl, thiazol-5-yl, thiazolin-2-yl, thiazolin-4-yl, thiazolin-5-yl, isothiazol-2-yl, isothiazol-4-yl, isothiazol-5-yl, isothiazolin-2-yl, isothiazolin-4-yl, isothiazolin-5-yl, each of which can be substituted by up to five radicals $R^{31}$ to $R^{35}$;

naphthyl or a benzo-fused 5- or 6-membered heteroaromatic having one to three heteroatoms from the group consisting of nitrogen, sulfur and oxygen in the ring, such as benzofuranyl, benzothienyl, 2,1,3-benzothiadiazolyl, indolyl, indazolyl, benzotriazolyl, 1,2,3-benzothiadiazolyl, benzoxazolyl, benzisoxazolyl, benzothiazolyl, benzisothiazolyl, quinolinyl, cinnolinyl, quinoxalinyl, phthalazinyl or benzofuroxanyl, which can be substituted by up to five radicals $R^{31}$ to $R^{35}$;

$A^5$ is a $C_2$–$C_6$-alkenyl, $C_3$–$C_8$-cycloalkenyl, $C_5$–$C_8$-cycloalkadienyl or $C_2$–$C_6$-alkynyl group, each of which can carry up to 7 substituents $R^{31}$ to $R^{37}$;

$A^6$ is a $C_1$–$C_8$-alkyl or $C_3$–$C_8$-cycloalkyl group, each of which can carry up to 7 substituents $R^{31}$ to $R^{37}$;

$R^{31}$, $R^{32}$, $R^{33}$, $R^{34}$, $R^{35}$, $R^{36}$ and $R^{37}$ are a) a $C_3$–$C_8$-cycloalkyl group which can carry one to three $C_1$–$C_4$-alkyl radicals;

b) a $C_1$–$C_8$-alkyl group which can carry one to five halogen atoms and/or one of the following radicals: $C_1$–$C_4$-alkoxy, $C_1$–$C_4$-haloalkoxy, particularly $C_1$–$C_2$-haloalkoxy, $C_1$–$C_4$-alkylthio, cyano, $C_3$–$C_8$-cycloalkyl or di-$C_1$–$C_4$-alkylamino;

c) a $C_1$–$C_8$-alkoxy group or a $C_3$–$C_5$-cycloalkoxy group, each of which can carry one to five halogen atoms and/or one of the following radicals: $C_1$–$C_4$-alkoxy, $C_1$–$C_4$-haloalkoxy, $C_1$–$C_4$-alkylthio, $C_3$–$C_8$-cycloalkyl or di-$C_1$–$C_4$-alkylamino;

d) a $C_1$–$C_4$-alkylthio group which can carry one to five halogen atoms and/or one of the following radicals: $C_1$–$C_4$-alkoxy, $C_1$–$C_4$-haloalkoxy, particularly $C_1$–$C_2$-haloalkoxy, $C_1$–$C_4$-alkylthio, $C_3$–$C_8$-cycloalkyl or di-$C_1$–$C_4$-alkylamino;

e) a di-$C_1$–$C_4$-alkylamino or a di-$C_1$–$C_4$-alkylaminoxy group, a $C_5$–$C_8$-cycloalkaniminoxy group or a $C_1$–$C_{10}$-alkaniminoxy group;

f) a $C_2$–$C_6$-alkenyl or a $C_2$–$C_6$-alkynyl group, which can carry one to five halogen atoms and/or one of the following radicals: $C_1$–$C_4$-alkoxy, $C_1$–$C_4$-haloalkoxy or $C_1$–$C_4$-alkylthio;

g) hydrogen;

h) nitro, halogen, cyano or tri-$C_1$–$C_4$-alkylsilyl;

Y is oxygen or sulfur.

The cyclic acetals where $A=A^1, A^2, A^3$ or $A^6$ are prepared by reacting the corresponding 6-hydroxybenzoic acids (for Y=O) or 6-mercaptobenzoic acids (for Y=S) with a compound $O=CR^1R^2$ in the presence of an acidic catalyst:

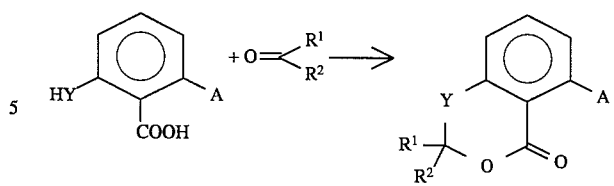

$(A=A^1, A^2, A^3$ or $A^6)$

The starting substances are generally known or accessible in a generally known manner.

To bind the water formed in the reaction a dehydrating agent can be added such as eg. molecular sieve, acid anhydrides, such as trifluoroacetic anhydride or acetic anhydride, or sodium sulfate or calcium chloride if this promotes the conversion. A reactive acetal of the compound $O=CR^1R^2$ is also suitable, such as eg. a dimethyl acetal, diethyl acetal, ethylene acetal or propylene acetal. Suitable catalysts are particularly acidic ion exchangers, protic acids such as eg. toluenesulfonic acid, sulfuric acid, phosphoric acid etc. or Lewis acids such as eg. aluminum chloride, titanium tetrachloride, zinc chloride, calcium chloride, magnesium chloride, tin chlorides etc. Often the water formed or the alcohol formed from the acetal can be removed directly from the reaction mixture by distillation. The cyclic acetals where $A=A^1$ can be further modified on the hydroxyl group by reacting them eg. with sulfonic anhydrides or sulfonyl halides (see synthesis examples). Cyclic acetals I where $A=A^4$ or $A^5$ are obtained particularly advantageously by reaction of compounds I where $A=A^2$ and compounds X-$A^4$ or X—$A^5$ in the presence of a catalytically active palladium compound according to the following reaction scheme:

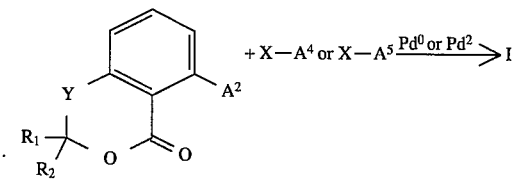

$R^1$, $R^2$, Y and $A^4$ or $A^5$ here have the meanings described above and $A^2$ is eg. chlorine, bromine, iodine, $C_1$–$C_4$-haloalkylsulfonyloxy, in particular trifluoromethylsulfonyloxy, $C_1$–$C_4$-alkylsulfonyloxy or fluorosulfonyloxy.

X is hydrogen, in particular if A is $A^5$, trialkylstannyl, eg. tri-C1–$C_8$-alkylstannyl such as trimethylstannyl, triethylstannyl, tripropylstannyl, tributylstannyl, tripentylstannyl or trihexylstannyl, dihydroxyboranyl, dialkoxyboranyl, eg. di-$C_1$–$C_4$-alkoxyboranyl such as dimethoxyboranyl, diethoxyboranyl, dipropoxyboranyl, diisopropoxyboranyl or dibutoxyboranyl or isomers or alkylenedioxyboranyl, eg. $C_1$–$C_4$-alkylenedioxyboranyl such as ethylenedioxyboranyl or 1,3-propylenedioxyboranyl. The boron or tin compounds used are either known or can be prepared similarly to known compounds.

A catalytically active palladium compound is employed in this novel process. Any desired palladium salts or complexes are suitable here which are at least partially soluble in the reaction mixture. The oxidation states of the palladium can be 0 or 2. In the palladium salts, the following counterions, inter alia, are suitable: chloride, bromide, iodide, sulfate, acetate, trifluoroacetate, acetylacetonate or hexafluoro-2,4-pentanedionate. Many different palladium complexes can be used. The only condition is that the ligands on the palladium can be displaced by the substrate under the reaction conditions. Phosphine ligands such as eg. arylalkylphosphines such as, inter alia, methyldiphenylphosphine, isopropyldiphenylphosphine, triarylphosphines such as, inter alia, triphenylphosphine, tritolylphosphine, trixylylphosphine, trihetarylphosphines such as trifurylphosphine or dimeric phosphines are particularly suitable. Olefinic ligands such as, inter alia, dibenzylideneacetone or its salts, cycloocta-1,5-diene or amines such as trialkylamines (eg. triethylamine, tetramethylethylenediamine, N-methylmorpholine) or pyridine are also highly suitable.

The complex used can be employed directly in the reaction. Thus the reaction can be carried out eg. with tetrakistriphenylphosphinepalladium(0), bistriphenylphosphinepalladium dichloride, bistriphenylphosphinepalladiumdiacetate, a dibenzylideneacetonepalladium(0) complex, tetrakismethyldiphenylphosphinepalladium(0) or bis(1,2-diphenylphosphinoethane)palladiumdichloride. A palladium salt and additionally a suitable ligand can also be used, which then only form the catalytically active complex in situ. This procedure suggests itself eg. with the abovementioned salts and phosphine ligands such as eg. trifurylphosphine or tritolylphosphine. Palladium complexes such as eg. tris(dibenzylideneacetone)dipalladium, bis(dibenzylideneacetone)palladium or 1,5-cyclooctadienepalladiumdichloride can also be further activated by the addition of ligands such as eg. trifurylphosphine or tritolylphosphine.

Customarily, from 0.001 to 10 mol %, in particular from 0.005 to 5 mol %, of the palladium compound (salt or complex) are used, based on the compound $X-A^4$ or $X-A^5$. Higher amounts are possible, but rather uneconomical.

The amount of $X-A^4$ or $X-A^5$, based on the starting substance $I-A^2$ (I where $A=A^2$), is in general from 0.8 to 3, preferably from 0.95 to 1.5, mole equivalents.

All solvents which do not react themselves with the substrates used are suitable for the reaction. Polar solvents accelerate the reaction. Ethers such as diethyl ether, methyl tert-butyl ether, dimethoxyethane, tetrahydrofuran and dioxane, amides such as dimethylformamide, dimethylacetamide, N-methylpyrrolidone and dimethylpropyleneurea or amines such as triethylamine are particularly suitable. The use of mixtures eg. of ethers with amides or mixtures of the abovementioned solvents with water or aliphatic alcohols is often advantageous. The addition of tetraalkylammonium halides or alkali metal halides such as eg. lithium chloride is often helpful and in particular to be recommended if $A^2$ is a sulfonyloxy radical.

If X is hydrogen, it is often advantageous to add an inorganic or organic base such as eg. calcium carbonate, sodium carbonate, sodium phosphate, potassium phosphate, sodium hydroxide, potassium hydroxide, calcium hydroxide, calcium carbonate, pyridine, triethylamine etc. to the reaction mixture.

The reaction temperature is from $-20°$ to $200°$ C., preferably from $50°$ to $160°$ C. The reaction times are customarily from a few minutes to 50 hours, usually 0.5–10 hours. When using low-boiling solvents it is sometimes useful to carry out the reaction under autogenous pressure in an autoclave.

If desired, the products of the formula I thus obtained where $A=A^4$ or $A^5$ can be converted by further reactions into other intermediates of the formula I where $A=A^4$ or $A^5$. It may thus be necessary to remove protective groups. For example, the compound No. 1.017 from Table 1 can be prepared by hydrolytic removal of the trimethylsilyl radical from compound No. 1.001 from Table 1 in the presence of tetrabutylammonium fluoride.

Another possibility for preparing the intermediates I where $A=A^4$ is offered by cycloaddition of cyclic acetals I where $A=A^5$ to a diene, heterodiene or 1,3-dipole according to the following reaction equation:

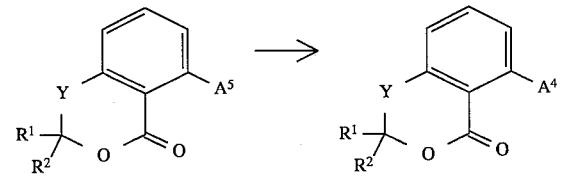

The alkenes and alkines described above are suitable for $A^5$; vinyl and ethynyl are very particularly preferred.

With respect to the (hetero)diene component and possible 1,3-dipolar compounds, reference may be made to G. March, Advanced Organic Chemistry, Second Edition, 1977, pp. 758–798.

Particularly preferred dienes are cyclopentadiene and 3-sulfolene. Nitrile oxides which are substituted by $R^{31}$ are particularly suitable as 1,3-dipoles. Various isoxazole and isoxazoline derivatives of the formula I are accessible in this manner (see Preparation Example No. 6).

The reaction times, reaction temperatures and solvents described above are also suitable here, nonpolar solvents such as hydrocarbons such as hexanes, heptanes or the like, aromatics such as toluene or chlorobenzene or chlorinated hydrocarbons additionally suggest themselves. In some cases it may be efficient to add a protic or Lewis acid as a catalyst.

The cyclic acetals I are herbicidally active themselves or are used foe preparing crop protection active compounds, eg. of the formula IV, by reaction with a salt $R^{50}$-M and a heterocycle III according to the following reaction scheme:

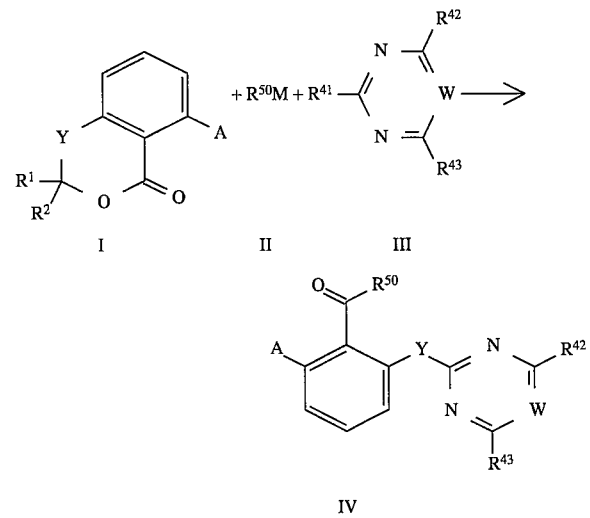

where $R^1$, $R^2$, Y and A have the meanings described above and the other radicals are:

M an alkali metal cation such as lithium, sodium, potassium or an equivalent of an alkaline earth metal cation such as magnesium, calcium or barium;

$R^{41}$ halogen such as fluorine, chlorine, bromine, iodine, alkylsulfonyl, particularly methylsulfonyl or haloalkylsulfonyl, particularly trifluoromethylsulfonyl;

$R^{50}$

9 a) a 5-membered heteroaromatic linked via a nitrogen atom, such as pyrrolyl, pyrazolyl, imidazolyl and triazolyl, which can carry one to two halogen atoms, in particular fluorine and chlorine, and/or one to two of the following radicals:
$C_1$–$C_4$-alkyl;
$C_1$–$C_4$-haloalkyl, in particular $C_1$–$C_2$-haloalkyl;
$C_1$–$C_4$-haloalkoxy, in particular $C_1$–$C_2$-haloalkoxy;
$C_1$–$C_4$-alkoxy;
$C_1$–$C_4$-alkylthio;

b) a radical —$(O)_m$—$NR^6R^7$ in which m is 0 or 1 and $R^6$ and $R^7$, which can be identical or different, have the following meanings:

hydrogen;

$C_1$–$C_8$-alkyl, in particular $C_1$–$C_4$-alkyl;

$C_3$–$C_6$-alkenyl, in particular 2-propenyl, 2-butenyl, 3-methyl-2-butenyl and 3-methyl-2-pentenyl;

$C_3$–$C_6$-alkynyl, preferably 2-propynyl, 2-butynyl, 1-methyl-2-propynyl and 1-methyl-2-butynyl, in particular 2-propynyl;

$C_3$–$C_8$-cycloalkyl, such as cyclopropyl, cyclobutyl, cyclopentyl, cyclohexyl, cycloheptyl and cyclooctyl, these alkyl, cycloalkyl, alkenyl and alkynyl groups each being able to carry one to five, in particular one to three, halogen atoms, preferably fluorine or chlorine and/or one to two of the following groups:

$C_1$–$C_4$-alkyl, $C_1$–$C_4$-alkoxy, $C_1$–$C_4$-alkylthio, $C_1$–$C_4$-haloalkoxy, $C_3$–$C_6$-alkenyloxy, $C_3$–$C_6$-alkenylthio, $C_3$–$C_6$-alkynyloxy, $C_3$–$C_6$-alkynylthio, where the alkenyl and alkynyl constituents present in these radicals preferably correspond to the abovementioned meanings;

$C_1$–$C_4$-alkylcarbonyl such as, in particular, methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$–$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl;

$C_3$–$C_6$-alkenylcarbonyl, $C_3$–$C_6$-alkynylcarbonyl, $C_3$–$C_6$-alkenyloxycarbonyl and $C_3$–$C_6$-alkynyloxycarbonyl, where the alkenyl and alkynyl radicals are preferably as defined above;

phenyl, which may be mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$alkylthio such as, for example, 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylpheny, 2,4-dimethoxyphenyl, 2-nitro-5-cyanophenyl, 2,6-difluorophenyl;

di-$C_1$–$C_4$-alkylamino such as, in particular, dimethylamino, diethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^6$ and $R^7$ are additionally phenyl, which can be substituted by one or more of the following radicals: halogen, nitro, cyano, $C_1$–$C_4$-alkyl, $C_1$–$C_4$-haloalkyl, in particular $C_1$–$C_2$-haloalkyl, $C_1$–$C_4$alkoxy, $C_1$–$C_4$-haloalkoxy, in particular $C_1$–$C_2$-haloalkoxy, or $C_1$–$C_4$-alkylthio;

10 or $R^6$ and $R^7$ together form an unsubstituted or substituted $C_4$–$C_7$-alkylene chain, which is closed to give a ring and can contain a heteroatom selected from the group consisting of oxygen, sulfur or nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_3)_3$—, —NH—$(CH_2)_3$—, —$CH_2$—NH—$(CH_2)_2$—, —$CH_2$—CH=CH—$CH_2$—, —CH=CH—$(CH_2)_3$—, where suitable substituents are in particular $C_1$–$C_4$-alkyl radicals;

c) additionally a group

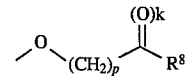

where k assumes the values 0, 1 or 2, p assumes the values 1, 2, 3 or 4 and $R^8$ is $C_1$–$C_4$-alkyl, $C_1$–$C_4$-haloalkyl, $C_3$–$C_6$-alkenyl, $C_3$–$C_6$-alkynyl or unsubstituted or substituted phenyl, as mentioned in particular for $R^6$ and $R^7$;

d) additionally a radical $OR^9$, where $R^9$ is:

i) $C_3$–$C_8$-cycloalkyl as mentioned above, which can carry one to three $C_1$–$C_4$-alkyl groups, in particular cyclopropyl, cyclopentyl, cyclohexyl, methylcyclohexyl;

ii) $C_1$–$C_8$-alkyl, which can carry one to five halogen atoms, in particular fluorine and chlorine and/or one of the following radicals:
$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, or phenyl or phenoxy mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, such as mentioned above in particular;

iii) a $C_1$–$C_8$-alkyl group, which can carry one to five, preferably one to three, halogen atoms, in particular fluorine and/or chlorine and carries one of the following radicals: a 5-membered heteroaromatic, containing one to three nitrogen atoms, or a 5-membered heteroaromatic, containing a nitrogen atom and an oxygen or sulfur atom, such as pyrazolyl, imidazolyl, benzimidazolyl, triazolyl, benzotriazolyl, isoxazolyl, oxazolyl, thiazolyl, bonded via a C atom or, if possible, an N atom, where the heteroaromatic can carry one to four halogen atoms and/or one to two of the following radicals:
nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5-yl, 3-tertbutylisoxazol-5-yl;

iv) a $C_2$–$C_6$-alkyl group, which in the 2-position carries one of the following radicals: $C_1$–$C_4$-alkoxyimino, $C_3$–$C_6$-alkynyloxyimino, $C_3$–$C_6$-haloalkenyloxyimino or benzyloxyimino;

v) a $C_3$–$C_6$-alkenyl group or a $C_3$–$C_6$-alkynyl group, where these groups in turn can carry one to five halogen atoms;

vi) $R^9$ additionally is a phenyl radical, which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, such as mentioned above in particular;

vii) a 5-membered heteroaromatic linked via a nitrogen atom, containing one to three nitrogen atoms, such as pyrazolyl, imidazolyl, benzimidazolyl, triazolyl, benzotriazolyl, preferably bonded via the 1-position, where the heteroaromatic can carry one to two halogen atoms and/or one to two of the following radicals:

$C_{-C4}$-alkyl, $C_1$–$C_4$-haloalkyl, $C_1$–$C_4$-alkoxy, phenyl, $C_{-C4}$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloroimidazol-1-yl;

viii) $R^9$ additionally is a group $-N=CR^{10}R^{11}$, where $R^{10}$ and $R^{11}$, which can be identical or different, are:

$C_1$–$C_{12}$-alkyl, $C_3$–$C_6$-alkenyl, $C_3$–$C_6$-alkynyl, $C_3$–$C_8$-cycloalkyl, where these radicals can carry a $C_1$–$C_4$-alkoxy, $C_1$–$C_4$-alkylthio and/or an unsubstituted or substituted phenyl radical, such as mentioned above in particular;

phenyl, which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

or $R^{10}$ and $R^{11}$ together form a $C_3$–$C_{12}$-alkylene chain, which can carry one to three $C_1$–$C_4$-alkyl groups and can contain a heteroatom from the group consisting of oxygen, sulfur and nitrogen, such as mentioned in particular in the case of $R^6$ and $R^7$.

e) or $R^{50}$ forms a radical $-NH-SO_2-R^{12}$, where $R^{12}$ is:
$C_1$–$C_4$-alkyl, $C_3$–$C_6$-alkenyl, $C_3$–$C_6$-alkynyl, $C_3$–$C_8$-cycloalkyl such as mentioned above in particular for $R^1$, where these radicals can carry a $C_1$–$C_4$-alkoxy or $C_1$–$C_4$-alkylthio radical and/or a phenyl radical as mentioned above;

phenyl, unsubstituted or substituted, in particular as mentioned above;

$R^{42}$ is the $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio groups and halogen atoms specifically mentioned above, in particular chlorine, methyl, methoxy, ethoxy, difluoromethoxy, trifluoromethoxy, particularly preferably methoxy;

W is nitrogen or $CR^{13}$, where $R^{13}$ is preferably hydrogen or together with $R^{43}$ forms a 4- to 5-membered alkylene or alkenylene chain in which one methylene group in each case is replaced by oxygen, such as $-CH_2-CH_2-O-$, $-CH=CH-O-$, $-CH_2-CH_2-CH_2-O-$, $-CH=CH-CH_2O-$, in particular hydrogen and $-CH_2-CH_2-O-$;

$R^{43}$ is halogen, $C_1$–$C_4$-alkyl, $C_1$–$C_4$-haloalkyl, particularly $C_1$–$C_2$-haloalkyl, $C_1$–$C_4$-alkoxy, $C_1$–$C_4$-haloalkoxy, particularly $C_1$–$C_2$-haloalkoxy, $C_1$–$C_4$-alkylthio groups, in particular chlorine, fluorine, methyl, methoxy, ethoxy, difluoromethoxy, trifluoromethoxy, particularly preferably methoxy, or, with $R^{13}$, is linked as mentioned above to give a 5- or 6-membered ring.

The reaction of the cyclic acetals I with the salt $R^{50}M$ and the further reaction with the heterocycle of the formula III can be carried out in one reaction vessel directly up to the active compound IV. In this case, the salt $R^{50}M$, which can also be prepared in situ from a compound $R^{50}H$ and a base, is added first and the heterocycle III is then added. III should advantageously only be added if the first step of the reaction, the addition of the salt $R^{50}M$ to the intermediate I, is largely completed. This can last from a few minutes to several hours, the reaction temperature being from $-40°$ C. to $200°$ C., usually from $0°$ C. to $130°$ C.

It is also possible to discontinue the reaction after the first stage and to isolate the intermediate V

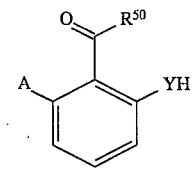

The compound V can then be reacted further by known processes, eg. as described in the Offenlegungsschrifts mentioned at the outset.

In both cases, the customary solvents are suitable provided they cannot be deprotonated themselves by the base used or the salt $R^{50}M$ and participate in the reaction. Polar solvents, eg. ethers such as diethyl ether, methyl tert-butyl ether, dimethoxyethane, tetrahydrofuran, dioxane, amides such as dimethylformamide, dimethylacetamide, N-methylpyrrolidone and dimethylpropyleneurea or dimethyl sulfoxide are particularly highly suitable. A phasetransfer catalyst such as a crown ether or a quaternary ammonium salt can be added if this promotes the conversion.

The reaction temperature is from $-40°$ to $200°$ C., preferably from 0 to $160°$ C. The reaction times are customarily from a few minutes to 50 hours, usually 0.5–10 hours.

In general, from 0.8 to 3, in particular 0.9 to 1.5, mole equivalents of the compound II ($R^{50}M$) are employed per mole of starting substance I. The amount of heterocycle III is likewise expediently from 0.8 to 3, in particular from 0.9 to 1.5 mole equivalents, based on I.

The reaction can be carried out continuously or batchwise, at atmospheric pressure, elevated pressure or reduced pressure.

There are a variety of working-up possibilities which individually depend on the solubility of the product in the solvents used and on the miscibility of the solvents with water and the boiling points of the solvents. Both aqueous and nonaqueous workups are possible.

A suitable working-up method consists, for example, in mixing the reaction mixture, from which the solvent can be partly or completely evaporated beforehand, with water and filtering out the product or extracting it with an organic solvent.

SYNTHESIS EXAMPLES

Example 1

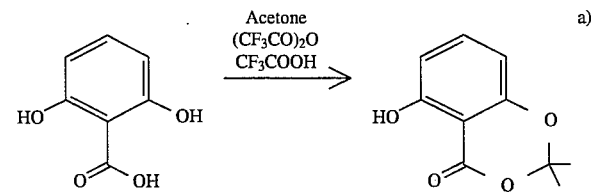

5-Hydroxy-2,2-dimethyl-4H-(1,3)benzodioxin-4-one 100 g (0.66 mol) of 2,6-dihydroxybenzoic acid are introduced into 800 ml of trifluoroacetic acid, and 100 ml of acetone and 216 g (1.98 mol) of trifluoroacetic anhydride are added. The mixture is refluxed for 2 h, and 50 ml of acetone per hour are then added dropwise for a further 5.5 h under reflux (total reaction time 7.5 h, total addition of acetone 375 ml). The reaction mixture is concentrated in vacuo at about 55° C., made up three times with toluene and concentrated again and the residue is finally dried for 1 h at 45° C. on an oil pump.

The oily product is taken up in 2 l of methyl tert-butyl ether, treated with 2 l of water and 2 l of saturated NaHCO$_3$ solution and stirred for about 1.5 h. The aqueous phase is separated off and extracted once with methyl tert-butyl ether, and the combined organic phases are washed with sodium chloride solution, dried and concentrated in vacuo. The residue is stirred with 200 ml of n-pentane, and the solid is filtered off with suction and dried in vacuo.

Yield: 115 g (90%)

M.p. 60°–62° C.

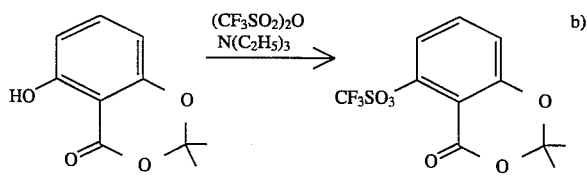

b)

2,2-Dimethyl-5-trifluoromethylsulfonyloxy-4H-(1,3)benzodioxin-4-one 80 g (0.41 mol) of 5-hydroxy-2,2-dimethyl-4H-(1,3)benzodioxin-4-one are dissolved in 1.5 l of methylene chloride, 129 g (1.28 mol) of triethylamine are added at 0° C. and 314 g (1.11 mol) of trifluoromethylsulfonic anhydride are then added dropwise in the course of 2 h. The mixture is allowed to warm to 10° C. and is subsequently stirred at this temperature for 10 min, and the mixture is then added with stirring to 1.5 l of water at 0° C. The organic phase is separated off and extracted with methylene chloride, and the combined organic phases are washed with water and saturated sodium chloride solution, dried over sodium sulfate and concentrated in vacuo. The residue is stirred with 200 ml of n-pentane, and the solid is filtered off, subsequently washed with n-pentane and dried at 40° C. on an oil pump.

Yield: 118 g (88%)

Melting point: 115° C.

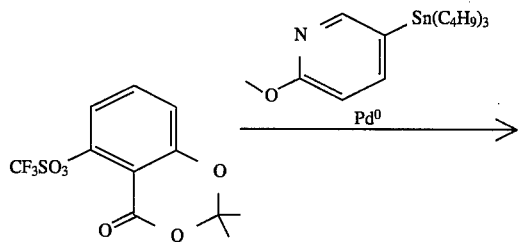

c)

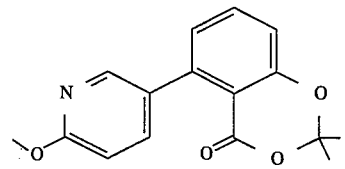

2,2-Dimethyl-5-(2-methoxypyridin-5-yl)-4H-(1,3)benzodioxin-4-one 8.7 g of 2,2-dimethyl-5-trifluoromethylsulfonyloxy-4H-(1,3)benzodioxin- 4-one, 23.2 g of 2-methoxy-5-tributyl-stannylpyridine, 3.4 g of lithium chloride, 0.6 g of tetrakistriphenylphosphine-palladium$^0$ and 70 mg of 2,6-di-t-butyl-4-methylphenol are dissolved in 150 ml of dioxane and the solution is stirred for 3 h at 140° C. in an autoclave. The mixture is concentrated in vacuo, stirred with 200 ml of n-pentane, filtered through a little silica gel 60 and subsequently washed with n-pentane, and the product is eluted with ethyl acetate. After concentration, 10.3 g of m.p. 160° C. remain.

d)
2-(4,6-Dimethoxypyrimidin-2-yloxy)-6-(2-methoxy-pyridin-5-yl)-benzoic acid acetone oxime ester 0.67 g of acetone oxime dissolved in 30 ml of toluene is treated with 1.66 g of a 30% strength sodium methoxide solution in methanol and the mixture is concentrated in vacuo. 35 ml of dimethylformamide and then 2.5 g of 2,2-dimethyl-5-(2-methoxypyridin-5-yl)-4H-(1,3)benzo-dioxin-4-one are added, the mixture is stirred at room temperature for 15 min and 1.9 g of 4,6-dimethoxy-2-methyl-sulfonylpyrimidine are finally added. The mixture is subsequently stirred overnight, poured into 300 ml of water and extracted with methyl t-butyl ether, and the organic phase is washed thoroughly with water and saturated sodium chloride solution, dried over sodium sulfate and concentrated in vacuo. The crude product is purified by chromatography on silica gel 60 using n-hexane/ethyl acetate.

$^1$H-NMR (CDCl$_3$): δ=1.65 (s); 1.95 (s); 3.85 (s); 3.98 (s); 5.78 (s); 6.77 (d); 7.3–7.7 (m); 8=25 (d).

Example 2 a) 2,2-Dimethyl-5-(6-methoxypyridin-2-yl)-4H-(1,3)benzodioxin-4-one 10.9 g of 2,2-dimethyl-5-trifluoromethylsulfonyloxy-4H-(1,3)-benzodioxin- 4-one, 16.0 g of 6-methoxy-2-tributyl-stannylpyridine, 4.25 g of lithium chloride, 0.78 g of tetrakistriphenylphosphinepalladium$^0$ and 40 mg of 2,6-di-t-butyl-4-methylphenol are dissolved in 120 ml of dioxane and the mixture is stirred for 4 h at 140° C. in an autoclave. It is concentrated in vacuo and the product is chromatographed on silica gel 60 using ethyl acetate/toluene. 9.1 g (95%) of a solid of m.p. 130°–132° C. are obtained.

b) Benzyl 2-(4,6-dimethoxypyrimidin-2-yloxy)-6-(6-methoxy-pyridin-2-yl)benzoate 1.36 g of benzyl alcohol dissolved in 50 ml of dimethylformamide are treated with 380 mg of sodium hydride (80% strength in liquid paraffin) and the mixture is subsequently stirred at room temperature for 1 h. 3.0 g of 2,2-dimethyl- 5-(6-methoxypyridin-2-yl)- 4H-(1,3)benzo-dioxin-4-one are added, the mixture is stirred at room temperature for 3 h and 2.65 g of 4,6-dimethoxy-2-methylsulfonylpyrimidine are finally added. The mixture is stirred at room temperature for 2 h, at 80° C. for 1.5 h and at 115° C. for 3 h, poured into ice-water containing phosphoric acid and extracted with ethyl acetate, and the extract is washed with water, dried over sodium sulfate and concentrated in vacuo. The crude product is purified by chromatography on silica gel 60 using cyclohexane/toluene/ethyl acetate.

$^1$H-NMR (CDCl$_3$): δ=3.80 (s); 3.89 (s); 5.02 (s); 5.72 (s); 6.67 (d); 6.9–7.7 (m).

Example 3 a)
2,2-Dimethyl-5-phenyl-4H-(1,3)benzodioxin-4-one 0.23 g (0.2 mmol) of tetrakistriphenylphosphinepalladium is added under nitrogen to a solution of 2.93 g (9 mmol) of 2,2-dimethyl- 5-trifluoromethylsulfonyloxy-4H-(1,3)benzo-dioxin-4-one in 50 ml of dimethylformamide, the mixture is stirred for a few minutes and 2.97 g (14 mmol) of potassium phosphate and 2.04 g (9.9 mmol) of diisopropyl phenylboronate are then added. The mixture is heated to 100° C. until conversion is complete (about 16 h). After cooling, the reaction solution is poured into a mixture of 250 ml of water and 6 g of orthophosphoric acid and extracted three times with methyl tert-butyl ether, and the combined organic phases are washed with water and saturated sodium chloride solution, dried over sodium sulfate and concentrated. 2.6 g of a dark oil remain, which is chromatographed on silica gel using toluene/acetone. 1.3 g (57%) of a colorless solid are obtained, m.p. 158°–163° C. (recrystallized from hexane).

b)

The compound described under a) can also be prepared similarly using 1.21 g (9 mmol) of phenylboronic acid instead of the boronic acid ester used above. Yield 1.7 g (74%), physical data and purification as under a).

Example 4

2,2-Dimethyl-5-(3,4-(ethylenedioxy)-1-phenyl)-4H-(1,3)benzodioxin-4-one 0.35 g (0.3 mmol) of tetrakistriphenylphosphinepalladium is added under nitrogen to a solution of 4.24 g (13.6 mmol) of 2,2-dimethyl- 5-trifluoromethylsulfonyloxy-4H-(1,3)benzodioxin-4-one in 50 ml of dimethylformamide, the mixture is stirred for a few minutes and 4.24 9 (20 mmol) of potassium phosphate and 2.70 g (15 mmol) of 3,4-(ethylenedioxy)-1-phenylboronic acid are then added. The mixture is heated at 100° C. until conversion is complete (about 16 h). After cooling, the reaction solution is poured into a mixture of 250 ml of water and 8 g of orthophosphoric acid and extracted three times with methyl tert-butyl ether, and the combined organic phases are washed with water and saturated sodium chloride solution, dried over sodium sulfate and concentrated. 7.6 9 of a dark oil remain, which is chromatographed on silica gel using toluene/acetone. A colorless oil is obtained; for NMR see Table 1, No. 1.040.

Example 5

2,2-Dimethyl-5-(3-methyl-3-buten-1-ynyl)-4H-(1,3)benzodioxin-4-one 0.64 g (0.92 mmol) of bistriphenylphosphinepalladium dichloride, 4.4ml (46 mmol) of 3-methyl-3-buten-1-yne and 24ml of triethylamine are added under nitrogen to a solution of 15.0 g (46 mmol) of 2,2-dimethyl-5-trifluoromethylsulfonyloxy-4H(1,3)benzodioxin-4-one in 150 ml of dimethylformamide. The mixture is heated at 115° C. for 0.5 h, a further 6.6 ml of 3-methyl- 3-buten-1-yne are then added at this temperature in the course of 1 h and the reaction solution is subsequently stirred for 15 min. After cooling, it is poured into 500 ml of water containing phosphoric acid (pH 3) at 0° C. and extracted with methyl tert-butyl ether, and the combined organic phases are carefully washed with water and saturated sodium chloride solution, dried over sodium sulfate and concentrated. 14 g of a dark oil remain, which is chromatographed on silica gel using n-hexane/ethyl acetate. 7.0 g of colorless crystals are obtained, m.p. 60° C. (cf. Table 1, No. 1.009).

Example 6

2,2-Dimethyl-5-(3-methylisoxazol-5-yl)-4H-(1,3)benzodioxin-4-one

A solution of 1-chloro-1-(N-hydroxyimino)ethane, which has a content of about 0.18 mol, in 210 ml of methyl tert-butyl ether is first prepared by chlorination of acetaldoxime with elemental chlorine.

53 ml of the solution of 1-chloro-1-(N-hydroxyimino)ethane 45 described above and 6.3 ml of triethylamine are added with stirring at 0° C. to a solution of 8.0 g of 2,2-dimethyl-5-(ethynyl)-4H-(1,3)benzodioxin-4-one in 400 ml of methyl tert-butyl ether, and the mixture is allowed to come to room temperature and is subsequently stirred overnight. A further 53 ml of the solution of 1-chloro-1-(N-hydroxyimino)ethane described above and 6.3 ml of triethylamine are added and the reaction solution is stirred at room-temperature for 24 h. It is then poured into water containing phosphoric acid (pH 4) at 0° C. and extracted with methyl tert-butyl ether, and the combined organic phases are carefully washed with water, dried over sodium sulfate and concentrated. 8.8 g of crude product remain, which is chromatographed on silica gel using n-hexane/ethyl acetate. 4.1 g of colorless crystals are obtained, m.p. 74° C. (cf. Table 1, No. 1.020).

Example 7 a)
5–Chloro-2,2-dimethyl-4H-[3,1]benzoxathiin-4-one 20 g (106 mmol) of 2-chloro-6-mercaptobenzoic acid, 26 ml (212 mmol) of 2,2-dimethoxypropane and 2 g of Amberlyst 15 (strongly acidic ion exchange resin) are refluxed in 1 l of toluene for 3 h. 100 ml are then distilled off in the course of 2 h, a further 10 ml of 2,2-dimethoxypropane are added, boiling is continued for a short time, and the mixture is stirred overnight at room temperature, filtered and concentrated in vacuo. Yield: 22.4 g (92%) of oil, $^1$H-NMR (CDCl$_3$) δ=1.82 (s); 7.18–7.40 (m).

b) 5-Chloro-2-phenyl-4H-[3,1]benzoxathiin-4-one can be prepared using benzaldehyde dimethyl acetal similarly to Example 7a (m.p. 97°–103° C.).

Example 8

2,2-Dimethyl-5-(pyridin-2-yl)-4H-(1,3)benzo-dioxin-4-one 6.0 g (18.4 mmol) of 2,2-dimethyl-5-trifluoromethylsulfonyloxy- 4H-(1,3)benzodioxin-4-one, 7.0 g (19.0 mmol) of 2-tributylstannylpyridine, 2.3 g (55.2 mmol) of lithium chloride and 420 mg (0.36 mmol) of tetrakistriphenylphosphinepalladium⁰ are dissolved in 60 ml of dioxane and 90 ml of dimethylformamide and the mixture is refluxed for 1.5 h (reaction temperature about 120° C.). It is stirred into 1.4 l of water at 0° C. and extracted with methyl tert-butyl ether, and the extract is washed with water and sodium chloride solution, dried over sodium sulfate and concentrated in vacuo. The residue is taken up in 60 ml of ethyl acetate, 8 g of potassium fluoride are added and the mixture is stirred overnight. The solid is filtered off and subsequently washed with plenty of ethyl acetate, and the filtrate is concentrated in vacuo. The crude product is purified by chromatography on silica gel 60 using hexane/ethyl acetate. Yield: 2.39 g (51%). Melting point: 142° C.

Example 9

2,2,2-Trifluoroethyl 2-(4,6-dimethoxypyrimidin-2-yloxy)-6-ethynyl-benzoate 2.0 g of 2,2,2-trifluoroethanol are introduced into 80 ml of dimethylformamide and 0.60 g of 80% strength sodium hydride is added at room temperature. After 1 h, a clear solution has formed and 5.0 g of 2,2-dimethyl-5-trimethylsilylethynyl-4H-(1,3)benzodioxin- 4-one are added at room temperature. After 20 min, 4.0 g of 4,6-dimethoxy-2-methylsulfonylpyrimidine are added and the reaction solution is stirred overnight at room temperature. It is then poured into 400 ml of water containing phosphoric acid (pH 3) at 0° C. and extracted with methyl tert-butyl ether, and the combined organic phases are washed with water, dried over sodium sulfate and concentrated. 6.4 g of crude product remain, which is chromatographed on silica gel using n-hexane/ethyl acetate. A colorless oil (1.2 g) is obtained. ¹H-NMR (CDCl₃): δ=3.33 (s); 3.83 (s); 4.55 (q); 5.80 (s); 7.25–7.50 (m).

Example 10

2,2-Dimethyl-5-(2-chloropyridin-4-yl)-4H-(1,3)benzo-dioxin-4-one a) 2,2-Dimethyl-5-(1-oxopyridin-4-yl)-4H-(1,3)benzo-dioxin-4-one 300 mg of 2,2-dimethyl-5-(pyridin-4-yl)-4H-(1,3)benzodioxin-4-one are introduced into 20 ml of methylene chloride, 260 mg of 3-chloroperbenzoic acid are added at room temperature and the reaction mixture is stirred overnight. It is worked up directly by chromatography on silica gel 60 using methylene chloride/methanol. Yield 200 mg. ¹H-NMR (CDCl₃): δ: 1.80 (s); 6.95 (d); 7.07 (d); 7.25 (d); 7.60 (t); 8.25 (d).

b) 2,2-Dimethyl-5-(2-chloropyridin-4-yl)-4H-(1,3)benzo-dioxin4-one 850 mg of 2,2-dimethyl-5-(1-oxopyridin-4-yl)-4H-(1, 3)benzodioxin- 4-one are introduced into 20 ml of POCl₃ and the mixture is stirred at 105° C. for 4 h. The volatile components are removed in vacuo, the residue is poured into a mixture of 50 ml of ice water and 30 ml of methyl tert-butyl ether, and the mixture is adjusted with sodium hydrogencarbonate solution to a pH of 7.5 and extracted with methyl tert-butyl ether. The extract is washed with sodium chloride solution, dried over sodium sulfate and concentrated in vauco. Yield: 490 mg. ¹H-NMR (CDCl₃): δ: 1.80 (s); 6.95 (d); 7.07 (d); 7.16 (d); 7.27 (s); 7.59 (t); 8.40 (d).

The compounds I shown in Table 1 can be prepared, for example, similarly to the synthesis examples indicated in each case.

TABLE 1

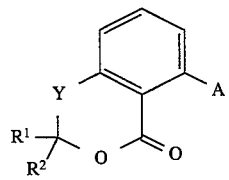

| No. | A | Method | R¹ | R² | Y | Physical data |
| --- | --- | --- | --- | --- | --- | --- |
| 1.001 | Trimethylsilylethynyl | 5 | CH₃ | CH₃ | O | δ (C): 0.30 (s); 1.72 (s); 6.93 (d); 7.32 (d); 7.47 (t). |
| 1.002 | 3,3-Dimethyl-1-butynyl | 5 | CH₃ | CH₃ | O | $n_D^{24}$ = 1.5365 |
| 1.003 | Phenylethynyl | 5 | CH₃ | CH₃ | O | M.p. = 101–102° C. |
| 1.004 | 3-Methoxy-1-propynyl | 5 | CH₃ | CH₃ | O | δ(C): 1.85 (s); 3.55 (s); 4.42 (s); 6.95 (d); 7.25 (d); 7.45 (t). |

TABLE 1-continued

| No. | A | Method | R¹ | R² | Y | Physical data |
|---|---|---|---|---|---|---|
| 1.005 | 3-(Dimethylamino)-1-pro-pynyl | 5 | $CH_3$ | $CH_3$ | O | M.p. = 59° C. |
| 1.006 | 1-Pentynyl | 5 | $CH_3$ | $CH_3$ | O | δ (C): 1.10 (t); 1.68 (mc); 1.70 (s); 2.50 (t); 6.87 (d); 7.20 (d); 7.40 (t). |
| 1.007 | Pyridin-2-yl | 1,2,8 | $CH_3$ | $CH_3$ | O | M.p. = 142° C. |
| 1.008 | Cyclohexylethynyl | 5 | $CH_3$ | $CH_3$ | O | M.p. = 60° C. |
| 1.009 | 3-Methyl-3-buten-1-ynyl | 5 | $CH_3$ | $CH_3$ | O | M.p. = 60° C. |
| 1.010 | Pyridin-4-yl | 1,2,8 | $CH_3$ | $CH_3$ | O | M.p. = 170° C. |
| 1.011 | 4-Methyloxazol-2-yl | 1,2,8 | $CH_3$ | $CH_3$ | O | M.p. = 159° C. |
| 1.012 | Pyridin-3-yl | 1,2,8 | $CH_3$ | $CH_3$ | O | M.p. = 172° C. |
| 1.013 | 5-Methyloxazol-2-yl | 1,2,8 | $CH_3$ | $CH_3$ | O | δ (C): 1.80 (s); 2.25 (s); 7.10 (d); 7.40 (d); 7.50 (s); 7.60 (t). |
| 1.014 | 3-(2-Propaniminoxy)-1-propynyl | 5 | $CH_3$ | $CH_3$ | O | M.p. = 73° C. |
| 1.015 | 3-(Morpholin-4-yl)-1-propynyl | 5 | $CH_3$ | $CH_3$ | O | M.p. = 79° C. |
| 1.016 | 4-(1,3-Dioxolan-2-yl)-3-methyl-3-buten-1-ynyl | 5 | $CH_3$ | $CH_3$ | O | M.p. = 110° C. |
| 1.017 | Ethynyl | 5 | $CH_3$ | $CH_3$ | O | M.p. = 76° C. |
| 1.018 | 6-Methylpyridin-2-yl | 1,2,8 | $CH_3$ | $CH_3$ | O | M.p. = 122° C. |
| 1.019 | 5-Methylpyridin-2-yl | 1,2,8 | $CH_3$ | $CH_3$ | O | M.p. = 127° C. |
| 1.020 | 3-Methylisoxazol-5-yl | 1,2,6,8 | $CH_3$ | $CH_3$ | O | M.p. = 74° C. |
| 1.021 | 1-Methylpyrrol-2-yl | 1,2,8 | $CH_3$ | $CH_3$ | O | δ (C): 1.77 (s); 3.42 (s); 6.13 (m); 6.25 (m); 6.75 (m); 6.97 (d); 7.10 (d); 7.53 (t). |
| 1.022 | 3-Ethylisoxazol-5-yl | 1,2,6,8 | $CH_3$ | $CH_3$ | O | M.p. = 105° C. |
| 1.023 | 2-Methoxypyridin-5-yl | 1,2,8 | $CH_3$ | $CH_3$ | O | M.p. = 160° C. |
| 1.024 | 2-Isopropoxypyridin-5-yl | 1,2,8 | $CH_3$ | $CH_3$ | O | M.p. = 178° C. |
| 1.025 | 2-Ethylthiopyridin-5-yl | 1,2,8 | $CH_3$ | $CH_3$ | O | δ (C): 1.40 (t); 1.80 (s); 3.21 (q); 7.00 (mc); 7.20 (d); 7.45–7.60 (m); 8.40 (d). |
| 1.026 | 2-Methylthiopyridin-5-yl | 1,2,8 | $CH_3$ | $CH_3$ | O | M.p. = 138° C. |
| 1.027 | 2-Ethoxypyridin-5-yl | 1,2,8 | $CH_3$ | $CH_3$ | O | M.p. = 170° C. |
| 1.028 | 3-Isopropylisoxazol-5-yl | 1,2,6,8 | $CH_3$ | $CH_3$ | O | M.p. = 78° C. |
| 1.029 | 2-Cyclopropylpyridin-4-yl | 1,2,8 | $CH_3$ | $CH_3$ | O | |
| 1.030 | 2-Cyclopropylpyridin-5-yl | 1,2,8 | $CH_3$ | $CH_3$ | O | |
| 1.031 | 12-Isopropylthiopyridin-5-yl | 1,2,8 | $CH_3$ | $CH_3$ | O | M.p. = 116° C. |
| 1.032 | Thiazol-4-yl | 1,2,8 | $CH_3$ | $CH_3$ | O | M.p. = 128–130° C. |
| 1.033 | Thiazol-5-yl | 1,2,8 | $CH_3$ | $CH_3$ | O | M.p. = 140–143° C. |
| 1.034 | Oxazol-2-yl | 1,2,8 | $CH_3$ | $CH_3$ | O | M.p. = 133–135° C. |
| 1.035 | Methyl | 1a,7 | H | t.-$C_4H_9$ | O | δ (D): 1.05 (s); |

TABLE 1-continued

| No. | A | Method | R¹ | R² | Y | Physical data |
|---|---|---|---|---|---|---|
| | | | | | | 2.60 (s); 5.40 (s); 7.05 (m); 7.52 (t). |
| 1.036 | Methyl | 1a,7 | H | C₆H₅ | O | M.p. = 105–115° C. |
| 1.037 | Bromine | 1a,7 | CH₃ | CH₃ | O | δ (D): 1.70 (s); 7.17 (d); 7.55 (m). |
| 1.038 | Bromine | 1a,7 | CH₃ | CH₃ | S | δ (D): 1.78 (s); 7.50 (m); 7.74 (d). |
| 1.039 | Phenyl | 1,2,8 | CH₃ | CH₃ | O | M.p. = 158–163° C. |
| 1.040 | 3,4-(Ethylene-dioxy)phenyl | 1,2,8 | CH₃ | CH₃ | O | δ (C): 1.77 (s); 4.27 (s); 6.75–7.00 (m); 7.48 (t). |
| 1.041 | 4-Formylphenyl | 1,2,8 | CH₃ | CH₃ | O | M.p. = 114–117° C. |
| 1.042 | 6-Methoxypyridin-2-yl | 1,2,8 | CH₃ | CH₃ | O | M.p. = 130–132° C. |
| 1.043 | 6-Methylthiopyridin-2-yl | 1,2,8 | CH₃ | CH₃ | O | M.p. = 134–135° C. |
| 1.044 | 6-Isopropoxypyridin-2-yl | 1,2,8 | CH₃ | CH₃ | O | M.p. = 132–133° C. |
| 1.045 | 6-Ethoxypyridin-2-yl | 1,2,8 | CH₃ | CH₃ | O | M.p. = 157–158° C. |
| 1.046 | 4-Methylpyridin-2-yl | 1,2,8 | CH₃ | CH₃ | O | M.p. = 110–115° C. |
| 1.047 | 6-Isopropylthiopyridin-2-yl | 1,2,8 | CH₃ | CH₃ | O | M.p. = 116–119° C. |
| 1.048 | 4,6-Dimethylpyridin-2-yl | 1,2,8 | CH₃ | CH₃ | O | M.p. = 128–129° C. |
| 1.049 | 3,5-Dimethylisoxazol-4-yl | 1,2,8 | CH₃ | CH₃ | O | δ (C): 1.78 (s); 2.12 (s); 2.30 (s); 6.87 (d); 7.05 (d); 7.57 (t). |
| 1.050 | 6-(2-Dimethylamino-ethoxy)-pyridin-2-yl | 1,2,8 | CH₃ | CH₃ | O | δ (C): 1.80 (s); 2.34 (s); 2.72 (t); 4.40 (t); 6.78 (d); 7.03 (d); 7.20 (d); 7.50–7.70 (m). |
| 1.051 | 3-Furyl | 1,2,8 | CH₃ | CH₃ | O | M.p. = 97° C. |
| 1.052 | 2-Furyl | 1,2,8 | CH₃ | CH₃ | O | |
| 1.053 | 2-Methyl-3-furyl | 1,2,8 | CH₃ | CH₃ | O | |
| 1.054 | 4-Methyl-3-furyl | 1,2,8 | CH₃ | CH₃ | O | |
| 1.055 | 3-Methyl-2-furyl | 1,2,8 | CH₃ | CH₃ | O | |
| 1.056 | 4-Methyl-2-furyl | 1,2,8 | CH₃ | CH₃ | O | |
| 1.057 | 5-Methyl-2-furyl | 1,2,8 | CH₃ | CH₃ | O | |
| 1.058 | 5-Methoxy-2-furyl | 1,2,8 | CH₃ | CH₃ | O | |
| 1.059 | 2-Thienyl | 1,2,8 | CH₃ | CH₃ | O | |
| 1.060 | 3-Thienyl | 1,2,8 | CH₃ | CH₃ | O | |
| 1.061 | 5-Methoxy-2-thienyl | 1,2,8 | CH₃ | CH₃ | O | |
| 1.062 | 4-Methoxy-2-thienyl | 1,2,8 | CH₃ | CH₃ | O | |
| 1.063 | 3-Methoxy-2-thienyl | 1,2,8 | CH₃ | CH₃ | O | |
| 1.064 | 5-Fluoro-2-thienyl | 1,2,8 | CH₃ | CH₃ | O | |
| 1.065 | 3-Fluoro-2-thienyl | 1,2,8 | CH₃ | CH₃ | O | |
| 1.066 | 4-Fluoro-2-thienyl | 1,2,8 | CH₃ | CH₃ | O | |
| 1.067 | 5-Methyl-2-thienyl | 1,2,8 | CH₃ | CH₃ | O | |
| 1.068 | 3-Methyl-2-thienyl | 1,2,8 | CH₃ | CH₃ | O | |
| 1.069 | 4-Methyl-2-thienyl | 1,2,8 | CH₃ | CH₃ | O | |
| 1.070 | 5-Methylthio-2-thienyl | 1,2,8 | CH₃ | CH₃ | O | |
| 1.071 | 3-Methylthio-2-thienyl | 1,2,8 | CH₃ | CH₃ | O | |
| 1.072 | 4-Methylthio-2-thienyl | 1,2,8 | CH₃ | CH₃ | O | |
| 1.073 | 5-Dimethyl- | 1,2,8 | CH₃ | CH₃ | O | |

TABLE 1-continued

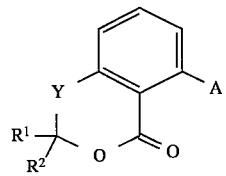

| No. | A | Method | R¹ | R² | Y | Physical data |
|---|---|---|---|---|---|---|
| 1.074 | 3-Dimethyl-amino-2-thienyl | 1,2,8 | CH₃ | CH₃ | O | |
| 1.075 | 4-Dimethyl-amino-2-thienyl | 1,2,8 | CH₃ | CH₃ | O | |
| 1.076 | 4,5-Dimethyl-2-thienyl | 1,2,8 | CH₃ | CH₃ | O | |
| 1.077 | 3,4-Dimethyl-2-thienyl | 1,2,8 | CH₃ | CH₃ | O | |
| 1.078 | 3,5-Dimethyl-2-thienyl | 1,2,8 | CH₃ | CH₃ | O | |
| 1.079 | 5-Methoxy-3-thienyl | 1,2,8 | CH₃ | CH₃ | O | |
| 1.080 | 4-Methoxy-3-thienyl | 1,2,8 | CH₃ | CH₃ | O | |
| 1.081 | 2-Methoxy-3-thienyl | 1,2,8 | CH₃ | CH₃ | O | |
| 1.082 | 5-Fluoro-3-thienyl | 1,2,8 | CH₃ | CH₃ | O | |
| 1.083 | 2-Fluoro-3-thienyl | 1,2,8 | CH₃ | CH₃ | O | |
| 1.084 | 4-Fluoro-3-thienyl | 1,2,8 | CH₃ | CH₃ | O | |
| 1.085 | 5-Methyl-3-thienyl | 1,2,8 | CH₃ | CH₃ | O | |
| 1.086 | 2-Methyl-3-thienyl | 1,2,8 | CH₃ | CH₃ | O | |
| 1.087 | 4-Methyl-3-thienyl | 1,2,8 | CH₃ | CH₃ | O | |
| 1.088 | 5-Methylthio-3-thienyl | 1,2,8 | CH₃ | CH₃ | O | |
| 1.089 | 2-Methylthio-3-thienyl | 1,2,8 | CH₃ | CH₃ | O | |
| 1.090 | 4-Methylthio-3-thienyl | 1,2,8 | CH₃ | CH₃ | O | |
| 1.091 | 5-Dimethyl-amino-3-thienyl | 1,2,8 | CH₃ | CH₃ | O | |
| 1.092 | 2-Dimethyl-amino-3-thienyl | 1,2,8 | CH₃ | CH₃ | O | |
| 1.093 | 4-Dimethyl-amino-3-thienyl | 1,2,8 | CH₃ | CH₃ | O | |
| 1.094 | 4,5-Dimethyl-3-thienyl | 1,2,8 | CH₃ | CH₃ | O | |
| 1.095 | 2,4-Dimethyl-3-thienyl | 1,2,8 | CH₃ | CH₃ | O | |
| 1.096 | 2,5-Dimethyl-3-thienyl | 1,2,8 | CH₃ | CH₃ | O | |
| 1.097 | Oxazol-4-yl | 1,2,8 | CH₃ | CH₃ | O | |
| 1.098 | Oxazol-5-yl | 1,2,8 | CH₃ | CH₃ | O | |
| 1.099 | 2-Methyloxazol-4-yl | 1,2,8 | CH₃ | CH₃ | O | |
| 1.100 | 2-Methyloxazol-5-yl | 1,2,8 | CH₃ | CH₃ | O | |
| 1.101 | 2-Ethyloxazol-4-yl | 1,2,8 | CH₃ | CH₃ | O | |
| 1.102 | 2-Ethyloxazol-5-yl | 1,2,8 | CH₃ | CH₃ | O | |
| 1.103 | 2-Methoxyoxazol-4-yl | 1,2,8 | CH₃ | CH₃ | O | |
| 1.104 | 2-Methoxyoxazol-5-yl | 1,2,8 | CH₃ | CH₃ | O | |
| 1.105 | 2-Methylthiooxazol-4-yl | 1,2,8 | CH₃ | CH₃ | O | |
| 1.106 | 2-Methylthioxazol-5-yl | 1,2,8 | CH₃ | CH₃ | O | |
| 1.107 | 2-Ethoxyoxazol-4-yl | 1,2,8 | CH₃ | CH₃ | O | |
| 1.108 | 2-Ethoxyoxazol-5-yl | 1,2,8 | CH₃ | CH₃ | O | |
| 1.109 | 5-Methyloxazol-4-yl | 1,2,8 | CH₃ | CH₃ | O | |
| 1.110 | 4-Methyloxazol-5-yl | 1,2,8 | CH₃ | CH₃ | O | |
| 1.111 | 5-Methyloxazol-4-yl | 1,2,8 | CH₃ | CH₃ | O | |
| 1.112 | 4-Methyloxazol-5-yl | 1,2,8 | CH₃ | CH₃ | O | |
| 1.113 | Isoxazol-3-yl | 1,2,8 | CH₃ | CH₃ | O | |
| 1.114 | Isoxazol-4-yl | 1,2,8 | CH₃ | CH₃ | O | |
| 1.115 | Isoxazol-5-yl | 1,2,8 | CH₃ | CH₃ | O | |
| 1.116 | 4-Methylisoxazol-3-yl | 1,2,8 | CH₃ | CH₃ | O | |
| 1.117 | 5-Methylisoxazol-3-yl | 1,2,8 | CH₃ | CH₃ | O | |
| 1.118 | 3-Methylisoxazol-4-yl | 1,2,8 | CH₃ | CH₃ | O | |
| 1.119 | 5-Methylisoxazol-4-yl | 1,2,8 | CH₃ | CH₃ | O | |
| 1.120 | 4-Trifluoromethylisox-azol-3-yl | 1,2,8 | CH₃ | CH₃ | O | |
| 1.121 | 5-Trifluoromethylisox-azol-3-yl | 1,2,8 | CH₃ | CH₃ | O | |
| 1.122 | 3-Trifluoromethylisox-azol-4-yl | 1,2,8 | CH₃ | CH₃ | O | |
| 1.123 | 5-Trifluoromethylisox-azol-4-yl | 1,2,8 | CH₃ | CH₃ | O | |
| 1.124 | 3-Trifluoromethylisox-azol-5-yl | 1,2,6,8 | CH₃ | CH₃ | O | |
| 1.125 | 4-Trifluoromethylisox-azol-5-yl | 1,2,8 | CH₃ | CH₃ | O | |
| 1.126 | 1,2,3-Oxadiazol-4-yl | 1,2,8 | CH₃ | CH₃ | O | |
| 1.127 | 1,2,3-Oxadiazol-5-yl | 1,2,8 | CH₃ | CH₃ | O | |
| 1.128 | 5-Methyl-1,2,3-oxa- | 1,2,8 | CH₃ | CH₃ | O | |

TABLE 1-continued

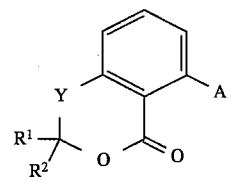

| No. | A | Method | R¹ | R² | Y | Physical data |
|---|---|---|---|---|---|---|
| | zol-4-yl | | | | | |
| 1.129 | 4-Methyl-1,2,3-oxa-diazol-5-yl | 1,2,8 | CH₃ | CH₃ | O | |
| 1.130 | 5-Fluoro-1,2,3-oxadiazol-4-yl | 1,2,8 | CH₃ | CH₃ | O | |
| 1.131 | 4-Fluoro-1,2,3-oxadiazol-5-yl | 1,2,8 | CH₃ | CH₃ | O | |
| 1.132 | 5-Trifluoromethyl-1,2,3-oxadiazol-4-yl | 1,2,8 | CH₃ | CH₃ | O | |
| 1.133 | 4-Trifluoromethyl-1,2,3-oxadiazol-5-yl | 1,2,8 | CH₃ | CH₃ | O | |
| 1.134 | 1,3,4-Oxadiazol-2-yl | 1,2,8 | CH₃ | CH₃ | O | |
| 1.135 | 5-Methyl-1,3,4-oxadiazol-2-yl | 1,2,8 | CH₃ | CH₃ | O | |
| 1.136 | 5-Trifluoromethyl-1,3,4-oxadiazol-2-yl | 1,2,8 | CH₃ | CH₃ | O | |
| 1.137 | 5-Methylthio-1,3,4-Oxadiazol-2-yl | 1,2,8 | CH₃ | CH₃ | O | |
| 1.138 | 1,2,4-Oxadiazol-3-yl | 1,2,8 | CH₃ | CH₃ | O | |
| 1.139 | 1,2,4-Oxadiazol-5-yl | 1,2,8 | CH₃ | CH₃ | O | |
| 1.140 | 5-Methyl-1,2,4-oxadiazol-3-yl | 1,2,8 | CH₃ | CH₃ | O | |
| 1.141 | 3-Methyl-1,2,4-oxadiazol-5-yl | 1,2,8 | CH₃ | CH₃ | O | |
| 1.142 | 5-Methoxy-1,2,4-oxadiazol-3-yl | 1,2,8 | CH₃ | CH₃ | O | |
| 1.143 | 3-Methoxy-1,2,4-oxadiazol-5-yl | 1,2,8 | CH₃ | CH₃ | O | |
| 1.144 | 5-Trifluoromethyl-1,2,4-oxadiazol-3-yl | 1,2,8 | CH₃ | CH₃ | O | |
| 1.145 | 3-Trifluoromethyl-1,2,4-oxadiazol-5-yl | 1,2,8 | CH₃ | CH₃ | O | |
| 1.146 | 1,2,5-Oxadiazol-3-yl | 1,2,8 | CH₃ | CH₃ | O | |
| 1.147 | 4-Methyl-1,2,5-oxadiazol-3-yl | 1,2,8 | CH₃ | CH₃ | O | |
| 1.148 | 4-Trifluoromethyl-1,2,5-oxadiazol-3-yl | 1,2,8 | CH₃ | CH₃ | O | |
| 1.149 | 1,2,3-Thiadiazol-4-yl | 1,2,8 | CH₃ | CH₃ | O | |
| 1.150 | 1,2,3-Thiadiazol-5-yl | 1,2,8 | CH₃ | CH₃ | O | |
| 1.151 | 5-Methyl-1,2,3-thiadiazol-4-yl | 1,2,8 | CH₃ | CH₃ | O | |
| 1.152 | 4-Methyl-1,2,3-thiadiazol-5-yl | 1,2,8 | CH₃ | CH₃ | O | |
| 1.153 | 5-Fluoro-1,2,3-thiadiazol-4-yl | 1,2,8 | CH₃ | CH₃ | O | |
| 1.154 | 4-Fluoro-1,2,3-thiadiazol-5-yl | 1,2,8 | CH₃ | CH₃ | O | |
| 1.155 | 5-Trifluoromethyl-1,2,3-thiadiazol-4-yl | 1,2,8 | CH₃ | CH₃ | O | |
| 1.156 | 4-Trifluoromethyl-1,2,3-thiadiazol-5-yl | 1,2,8 | CH₃ | CH₃ | O | |
| 1.157 | 1,3,4-Thiadiazol-2-yl | 1,2,8 | CH₃ | CH₃ | O | |
| 1.158 | 5-Methyl-1,3,4-thiadiazol-2-yl | 1,2,8 | CH₃ | CH₃ | O | |
| 1.159 | 5-Trifluoromethyl-1,3,4-thiadiazol-2-yl | 1,2,8 | CH₃ | CH₃ | O | |
| 1.160 | 5-Methylthio-1,3,4-thiadiazol-2-yl | 1,2,8 | CH₃ | CH₃ | O | |
| 1.161 | 1,2,4-Thiadiazol-3-yl | 1,2,8 | CH₃ | CH₃ | O | |
| 1.162 | 1,2,4-Thiadiazol-5-yl | 1,2,8 | CH₃ | CH₃ | O | |
| 1.163 | 5-Methyl-1,2,4-thiadiazol-3-yl | 1,2,8 | CH₃ | CH₃ | O | |
| 1.164 | 3-Methyl-1,2,4-thiadiazol-5-yl | 1,2,8 | CH₃ | CH₃ | O | |
| 1.165 | 5-Methoxy-1,2,4-thiadiazol-3-yl | 1,2,8 | CH₃ | CH₃ | O | |
| 1.166 | 3-Methoxy-1,2,4-thiadi- | 1,2,8 | CH₃ | CH₃ | O | |

TABLE 1-continued

| No. | A | Method | R¹ | R² | Y | Physical data |
|---|---|---|---|---|---|---|
| | azol-5-yl | | | | | |
| 1.167 | 5-Trifluoromethyl-1,2,4-thiadiazol-3-yl | 1,2,8 | CH₃ | CH₃ | O | |
| 1.168 | 3-Trifluoromethyl-1,2,4-thiadiazol-5-yl | 1,2,8 | CH₃ | CH₃ | O | |
| 1.169 | 1,2,5-Thiadiazol-3-yl | 1,2,8 | CH₃ | CH₃ | O | |
| 1.170 | 4-Methyl-1,2,5-thiadiazol-3-yl | 1,2,8 | CH₃ | CH₃ | O | |
| 1.171 | 4-Trifluoromethyl-1,2,5-thiadiazol-3-yl | 1,2,8 | CH₃ | CH₃ | O | |
| 1.172 | Thiazol-2-yl | 1,2,8 | CH₃ | CH₃ | O | |
| 1.173 | 4-Methylthiazol-2-yl | 1,2,8 | CH₃ | CH₃ | O | |
| 1.174 | 5-Methylthiazol-2-yl | 1,2,8 | CH₃ | CH₃ | O | |
| 1.175 | 4-Methylthiazol-5-yl | 1,2,8 | CH₃ | CH₃ | O | |
| 1.176 | 5-Methylthiazol-4-yl | 1,2,8 | CH₃ | CH₃ | O | |
| 1.177 | 2-Methylthiazol-4-yl | 1,2,8 | CH₃ | CH₃ | O | |
| 1.178 | 2-Methylthiazol-5-yl | 1,2,8 | CH₃ | CH₃ | O | |
| 1.179 | 4-Methoxythiazol-2-yl | 1,2,8 | CH₃ | CH₃ | O | |
| 1.180 | 5-Methoxythiazol-2-yl | 1,2,8 | CH₃ | CH₃ | O | |
| 1.181 | 4-Methoxythiazol-5-yl | 1,2,8 | CH₃ | CH₃ | O | |
| 1.182 | 5-Methoxythiazol-4-yl | 1,2,8 | CH₃ | CH₃ | O | |
| 1.183 | 2-Methoxythiazol-4-yl | 1,2,8 | CH₃ | CH₃ | O | |
| 1.184 | 2-Methoxythiazol-5-yl | 1,2,8 | CH₃ | CH₃ | O | |
| 1.185 | 4-Trifluoromethylthiazol-2-yl | 1,2,8 | CH₃ | CH₃ | O | |
| 1.186 | 5-Trifluoromethylthiazol-2-yl | 1,2,8 | CH₃ | CH₃ | O | |
| 1.187 | 4-Trifluoromethylthiazol-5-yl | 1,2,8 | CH₃ | CH₃ | O | |
| 1.188 | 5-Trifluoromethylthiazol-4-yl | 1,2,8 | CH₃ | CH₃ | O | |
| 1.189 | 2-Trifluoromethylthiazol-4-yl | 1,2,8 | CH₃ | CH₃ | O | |
| 1.190 | 2-Trifluoromethylthiazol-5-yl | 1,2,8 | CH₃ | CH₃ | O | |
| 1.191 | 4-Methylthiothiazol-2-yl | 1,2,8 | CH₃ | CH₃ | O | |
| 1.192 | 5-Methylthiothiazol-2-yl | 1,2,8 | CH₃ | CH₃ | O | |
| 1.193 | 4-Methylthiothiazol-5-yl | 1,2,8 | CH₃ | CH₃ | O | |
| 1.194 | 5-Methylthiothiazol-4-yl | 1,2,8 | CH₃ | CH₃ | O | |
| 1.195 | 2-Methylthiothiazol-4-yl | 1,2,8 | CH₃ | CH₃ | O | |
| 1.196 | 2-Methylthiothiazol-5-yl | 1,2,8 | CH₃ | CH₃ | O | |
| 1.197 | Isothiazol-3-yl | 1,2,8 | CH₃ | CH₃ | O | |
| 1.198 | Isothiazol-4-yl | 1,2,8 | CH₃ | CH₃ | O | |
| 1.199 | Isothiazol-5-yl | 1,2,8 | CH₃ | CH₃ | O | |
| 1.200 | 5-Methylisothiazol-3-yl | 1,2,8 | CH₃ | CH₃ | O | |
| 1.201 | 4-Methylisothiazol-3-yl | 1,2,8 | CH₃ | CH₃ | O | |
| 1.202 | 5-Methylisothiazol-4-yl | 1,2,8 | CH₃ | CH₃ | O | |
| 1.203 | 3-Methylisothiazol-4-yl | 1,2,8 | CH₃ | CH₃ | O | |
| 1.204 | 3-Methylisothiazol-5-yl | 1,2,8 | CH₃ | CH₃ | O | δ (C): 1.79 (s); 2.54 (s); 7.00–7.15 (m); 7.55 (t). |
| 1.205 | 4-Methylisothiazol-5-yl | 1,2,8 | CH₃ | CH₃ | O | |
| 1.206 | 5-Methylthioisothiazol-3-yl | 1,2,8 | CH₃ | CH₃ | O | |
| 1.207 | 4-Methylthioisothiazol-3-yl | 1,2,8 | CH₃ | CH₃ | O | |
| 1.208 | 5-Methylthioisothiazol-4-yl | 1,2,8 | CH₃ | CH₃ | O | |
| 1.209 | 3-Methylthioisothiazol-4-yl | 1,2,8 | CH₃ | CH₃ | O | |
| 1.210 | 3-Methylthioisothiazol-5-yl | 1,2,8 | CH₃ | CH₃ | O | |
| 1.211 | 4-Methylthioisothiazol-5-yl | 1,2,8 | CH₃ | CH₃ | O | |
| 1.212 | 5-Methoxyisothiazol-3-yl | 1,2,8 | CH₃ | CH₃ | O | |

TABLE 1-continued

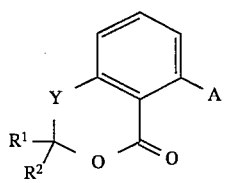

| No. | A | Method | $R^1$ | $R^2$ | Y | Physical data |
|---|---|---|---|---|---|---|
| 1.213 | 4-Methoxyisothiazol-3-yl | 1,2,8 | $CH_3$ | $CH_3$ | O | |
| 1.214 | 5-Methoxyisothiazol-4-yl | 1,2,8 | $CH_3$ | $CH_3$ | O | |
| 1.215 | 3-Methoxyisothiazol-4-yl | 1,2,8 | $CH_3$ | $CH_3$ | O | |
| 1.216 | 3-Methoxyisothiazol-5-yl | 1,2,8 | $CH_3$ | $CH_3$ | O | |
| 1.217 | 4-Methoxyisothiazol-5-yl | 1,2,8 | $CH_3$ | $CH_3$ | O | |
| 1.218 | 5-Trifluoromethyliso-thiazol-3-yl | 1,2,8 | $CH_3$ | $CH_3$ | O | |
| 1.219 | 4-Trifluoromethyliso-thiazol-3-yl | 1,2,8 | $CH_3$ | $CH_3$ | O | |
| 1.220 | 5-Trifluoromethyliso-thiazol-4-yl | 1,2,8 | $CH_3$ | $CH_3$ | O | |
| 1.221 | 3-Trifluoromethyliso-thiazol-4-yl | 1,2,8 | $CH_3$ | $CH_3$ | O | |
| 1.222 | 3-Trifluoromethyliso-thiazol-5-yl | 1,2,8 | $CH_3$ | $CH_3$ | O | |
| 1.223 | 4-Trifluoromethyliso-thiazol-5-yl | 1,2,8 | $CH_3$ | $CH_3$ | O | |
| 1.224 | 4-Chloroisothiazol-5-yl | 1,2,8 | $CH_3$ | $CH_3$ | O | |
| 1.225 | 4-Fluoroisothiazol-5-yl | 1,2,8 | $CH_3$ | $CH_3$ | O | |
| 1.226 | 4-Fluoro-3-methyliso-thiazol-5-yl | 1,2,8 | $CH_3$ | $CH_3$ | O | |
| 1.227 | 1-Methylpyrrol-2-yl | 1,2,8 | $CH_3$ | $CH_3$ | O | |
| 1.228 | 1-Methylpyrrol-3-yl | 1,2,8 | $CH_3$ | $CH_3$ | O | |
| 1.229 | 1-Ethylpyrrol-2-yl | 1,2,8 | $CH_3$ | $CH_3$ | O | |
| 1.230 | 1-Ethylpyrrol-3-yl | 1,2,8 | $CH_3$ | $CH_3$ | O | |
| 1.231 | 1-Phenylpyrrol-2-yl | 1,2,8 | $CH_3$ | $CH_3$ | O | |
| 1.232 | 1-Phenylpyrrol-3-yl | 1,2,8 | $CH_3$ | $CH_3$ | O | |
| 1.233 | Pyrazol-3-yl | 1,2,8 | $CH_3$ | $CH_3$ | O | |
| 1.234 | Pyrazol-4-yl | 1,2,8 | $CH_3$ | $CH_3$ | O | |
| 1.235 | Pyrazol-5-yl | 1,2,8 | $CH_3$ | $CH_3$ | O | |
| 1.236 | 1-Methylpyrazol-3-yl | 1,2,8 | $CH_3$ | $CH_3$ | O | |
| 1.237 | 1-Methylpyrazol-4-yl | 1,2,8 | $CH_3$ | $CH_3$ | O | |
| 1.238 | 1-Methylpyrazol-5-yl | 1,2,8 | $CH_3$ | $CH_3$ | O | |
| 1.239 | 4-Methylpyrazol-3-yl | 1,2,8 | $CH_3$ | $CH_3$ | O | |
| 1.240 | 5-Methylpyrazol-3-yl | 1,2,8 | $CH_3$ | $CH_3$ | O | |
| 1.241 | 3-Methylpyrazol-4-yl | 1,2,8 | $CH_3$ | $CH_3$ | O | |
| 1.242 | 5-Methylpyrazol-4-yl | 1,2,8 | $CH_3$ | $CH_3$ | O | |
| 1.243 | 3-Methylpyrazol-5-yl | 1,2,8 | $CH_3$ | $CH_3$ | O | |
| 1.244 | 4-Methylpyrazol-5-yl | 1,2,8 | $CH_3$ | $CH_3$ | O | |
| 1.245 | 1,4-Dimethylpyrazol-3-yl | 1,2,8 | $CH_3$ | $CH_3$ | O | |
| 1.246 | 1,5-Dimethylpyrazol-3-yl | 1,2,8 | $CH_3$ | $CH_3$ | O | |
| 1.247 | 1,3-Dimethylpyrazol-4-yl | 1,2,8 | $CH_3$ | $CH_3$ | O | |
| 1.248 | 1,5-Dimethylpyrazol-4-yl | 1,2,8 | $CH_3$ | $CH_3$ | O | |
| 1.249 | 1,3-Dimethylpyrazol-5-yl | 1,2,8 | $CH_3$ | $CH_3$ | O | |
| 1.250 | 1,4-Dimethylpyrazol-5-yl | 1,2,8 | $CH_3$ | $CH_3$ | O | |
| 1.251 | 1-Phenylpyrazol-3-yl | 1,2,8 | $CH_3$ | $CH_3$ | O | |
| 1.252 | 1-Phenylpyrazol-4-yl | 1,2,8 | $CH_3$ | $CH_3$ | O | |
| 1.253 | 1-Phenylpyrazol-5-yl | 1,2,8 | $CH_3$ | $CH_3$ | O | |
| 1.254 | 4-Phenylpyrazol-3-yl | 1,2,8 | $CH_3$ | $CH_3$ | O | |
| 1.255 | 5-Phenylpyrazol-3-yl | 1,2,8 | $CH_3$ | $CH_3$ | O | |
| 1.256 | 3-Phenylpyrazol-4-yl | 1,2,8 | $CH_3$ | $CH_3$ | O | |
| 1.257 | 5-Phenylpyrazol-4-yl | 1,2,8 | $CH_3$ | $CH_3$ | O | |
| 1.258 | 3-Phenylpyrazol-5-yl | 1,2,8 | $CH_3$ | $CH_3$ | O | |
| 1.259 | 4-Phenylpyrazol-5-yl | 1,2,8 | $CH_3$ | $CH_3$ | O | |
| 1.260 | 1-Phenyl-4-methyl-pyrazol-3-yl | 1,2,8 | $CH_3$ | $CH_3$ | O | |
| 1.261 | 1-Phenyl-5-methyl-pyrazol-3-yl | 1,2,8 | $CH_3$ | $CH_3$ | O | |
| 1.262 | 1-Phenyl-3-methyl-pyrazol-4-yl | 1,2,8 | $CH_3$ | $CH_3$ | O | |
| 1.263 | 1-Phenyl-5-methyl-pyrazol-4-yl | 1,2,8 | $CH_3$ | $CH_3$ | O | |
| 1.264 | 1-Phenyl-3-methyl-pyrazol-5-yl | 1,2,8 | $CH_3$ | $CH_3$ | O | |
| 1.265 | 1-Phenyl-4-methyl-pyrazol-5-yl | 1,2,8 | $CH_3$ | $CH_3$ | O | |
| 1.266 | 1-Methoxypyrazol-3-yl | 1,2,8 | $CH_3$ | $CH_3$ | O | |

TABLE 1-continued

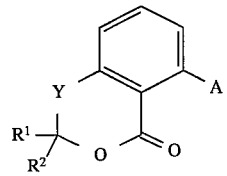

| No. | A | Method | $R^1$ | $R^2$ | Y | Physical data |
|---|---|---|---|---|---|---|
| 1.267 | 1-Methoxypyrazol-4-yl | 1,2,8 | $CH_3$ | $CH_3$ | O | |
| 1.268 | 1-Methoxypyrazol-5-yl | 1,2,8 | $CH_3$ | $CH_3$ | O | |
| 1.269 | 4-Fluoropyrazol-3-yl | 1,2,8 | $CH_3$ | $CH_3$ | O | |
| 1.270 | 5-Fluoropyrazol-3-yl | 1,2,8 | $CH_3$ | $CH_3$ | O | |
| 1.271 | 3-Fluoropyrazol-4-yl | 1,2,8 | $CH_3$ | $CH_3$ | O | |
| 1.272 | 5-Fluoropyrazol-4-yl | 1,2,8 | $CH_3$ | $CH_3$ | O | |
| 1.273 | 3-Fluoropyrazol-5-yl | 1,2,8 | $CH_3$ | $CH_3$ | O | |
| 1.274 | 4-Fluoropyrazol-5-yl | 1,2,8 | $CH_3$ | $CH_3$ | O | |
| 1.275 | 4-Fluoro-1-methyl-pyrazol-3-yl | 1,2,8 | $CH_3$ | $CH_3$ | O | |
| 1.276 | 5-Fluoro-1-methyl-pyrazol-3-yl | 1,2,8 | $CH_3$ | $CH_3$ | O | |
| 1.277 | 3-Fluoro-1-methyl-pyrazol-4-yl | 1,2,8 | $CH_3$ | $CH_3$ | O | |
| 1.278 | 5-Fluoro-1-methyl-pyrazol-4-yl | 1,2,8 | $CH_3$ | $CH_3$ | O | |
| 1.279 | 3-Fluoro-1-methyl-pyrazol-5-yl | 1,2,8 | $CH_3$ | $CH_3$ | O | |
| 1.280 | 4-Fluoro-1-methyl-pyrazol-5-yl | 1,2,8 | $CH_3$ | $CH_3$ | O | |
| 1.281 | 4-Trifluoromethyl-1-methyl-pyrazol-3-yl | 1,2,8 | $CH_3$ | $CH_3$ | O | |
| 1.282 | 5-Trifluoromethyl-1-methyl-pyrazol-3-yl | 1,2,8 | $CH_3$ | $CH_3$ | O | |
| 1.283 | 3-Trifluoromethyl-1-methyl-pyrazol-4-yl | 1,2,8 | $CH_3$ | $CH_3$ | O | |
| 1.284 | 5-Trifluoromethyl-1-methyl-pyrazol-4-yl | 1,2,8 | $CH_3$ | $CH_3$ | O | |
| 1.285 | 3-Trifluoromethyl-1-methyl-pyrazol-5-yl | 1,2,8 | $CH_3$ | $CH_3$ | O | |
| 1.286 | 4-Trifluoromethyl-1-methyl-pyrazol-5-yl | 1,2,8 | $CH_3$ | $CH_3$ | O | |
| 1.287 | Imidazol-2-yl | 1,2,8 | $CH_3$ | $CH_3$ | O | |
| 1.288 | Imidazol-4-yl | 1,2,8 | $CH_3$ | $CH_3$ | O | |
| 1.289 | 1-Methylimidazol-2-yl | 1,2,8 | $CH_3$ | $CH_3$ | O | |
| 1.290 | 1-Methylimidazol-4-yl | 1,2,8 | $CH_3$ | $CH_3$ | O | |
| 1.291 | 1-Methylimidazol-5-yl | 1,2,8 | $CH_3$ | $CH_3$ | O | |
| 1.292 | 4-Methylimidazol-2-yl | 1,2,8 | $CH_3$ | $CH_3$ | O | |
| 1.293 | 2-Methylimidazol-4-yl | 1,2,8 | $CH_3$ | $CH_3$ | O | |
| 1.294 | 5-Methylimidazol-4-yl | 1,2,8 | $CH_3$ | $CH_3$ | O | |
| 1.295 | 4-Methylimidazol-5-yl | 1,2,8 | $CH_3$ | $CH_3$ | O | |
| 1.296 | 1,4-Dimethyl-imidazol-2-yl | 1,2,8 | $CH_3$ | $CH_3$ | O | |
| 1.297 | 1,3-Dimethyl-imidazol-2-yl | 1,2,8 | $CH_3$ | $CH_3$ | O | |
| 1.298 | 1,2-Dimethyl-imidazol-4-yl | 1,2,8 | $CH_3$ | $CH_3$ | O | |
| 1.299 | 1,5-Dimethyl-imidazol-4-yl | 1,2,8 | $CH_3$ | $CH_3$ | O | |
| 1.300 | 1,2-Dimethyl-imidazol-5-yl | 1,2,8 | C83 | $CH_3$ | O | |
| 1.301 | 1,4-Dimethyl-imidazol-5-yl | 1,2,8 | $CH_3$ | $CH_3$ | O | |
| 1.302 | 1-Phenylimidazol-2-yl | 1,2,8 | $CH_3$ | $CH_3$ | O | |
| 1.303 | 1-Phenylimidazol-4-yl | 1,2,8 | $CH_3$ | $CH_3$ | O | |
| 1.304 | 1-Phenylimidazol-5-yl | 1,2,8 | $CH_3$ | $CH_3$ | O | |
| 1.305 | 1,2,3-Triazol-4-yl | 1,2,8 | $CH_3$ | $CH_3$ | O | |
| 1.306 | 1,2,4-Triazol-3-yl | 1,2,8 | $CH_3$ | $CH_3$ | O | |
| 1.307 | 1-Methyl-1,2,3-tri-azol-4-yl | 1,2,8 | $CH_3$ | $CH_3$ | O | |
| 1.308 | 1-Methyl-1,2,3-tri- | 1,2,8 | $CH_3$ | $CH_3$ | O | |

TABLE 1-continued

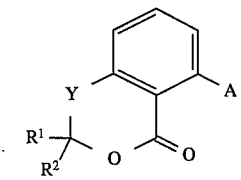

| No. | A | Method | R¹ | R² | Y | Physical data |
|---|---|---|---|---|---|---|
| | azol-5-yl | | | | | |
| 1.307 | 2-Methyl-1,2,3-triazol-4-yl | 1,2,8 | $CH_3$ | $CH_3$ | O | |
| 1.308 | 2,4-Dimethyl-1,2,3-triazol-5-yl | 1,2,8 | $CH_3$ | $CH_3$ | O | |
| 1.309 | 1,4-Dimethyl-1,2,3-triazol-5-yl | 1,2,8 | $CH_3$ | $CH_3$ | O | |
| 1.310 | 1,5-Dimethyl-1,2,3-triazol-4-yl | 1,2,8 | $CH_3$ | $CH_3$ | O | |
| 1.311 | 1-Methyl-1,2,4-triazol-3-yl | 1,2,8 | $CH_3$ | $CH_3$ | O | |
| 1.312 | 1-Methyl-1,2,4-triazol-5-yl | 1,2,8 | $CH_3$ | $CH_3$ | O | |
| 1.313 | 4-Methyl-1,2,4-triazol-3-yl | 1,2,8 | $CH_3$ | $CH_3$ | O | |
| 1.314 | 1,3-Dimethyl-1,2,4-triazol-5-yl | 1,2,8 | $CH_3$ | $CH_3$ | O | |
| 1.315 | 1,5-Dimethyl-1,2,4-triazol-3-yl | 1,2,8 | $CH_3$ | $CH_3$ | O | |
| 1.316 | 3,4-Dimethyl-1,2,4-triazol-5-yl | 1,2,8 | $CH_3$ | $CH_3$ | O | |
| 1.317 | 1-Trifluoromethyl-1,2,4-triazol-3-yl | 1,2,8 | $CH_3$ | $CH_3$ | O | |
| 1.318 | 1-Trifluoromethyl-1,2,4-triazol-5-yl | 1,2,8 | $CH_3$ | $CH_3$ | O | |
| 1.319 | 4-Trifluoromethyl-1,2,4-triazol-3-yl | 1,2,8 | $CH_3$ | $CH_3$ | O | |
| 1.320 | Tetrazol-5-yl | 1,2,8 | $CH_3$ | $CH_3$ | O | |
| 1.321 | 2-Methylpyridin-4-yl | 1,2,8 | $CH_3$ | $CH_3$ | O | |
| 1.322 | 3-Methylpyridin-4-yl | 1,2,8 | $CH_3$ | $CH_3$ | O | |
| 1.323 | 2,3-Dimethylpyridin-4-yl | 1,2,8 | $CH_3$ | $CH_3$ | O | |
| 1.324 | 2,6-Dimethylpyridin-4-yl | 1,2,8 | $CH_3$ | $CH_3$ | O | |
| 1.325 | 2,5-Dimethylpyridin-4-yl | 1,2,8 | $CH_3$ | $CH_3$ | O | |
| 1.326 | 3,5-Dimethylpyridin-4-yl | 1,2,8 | $CH_3$ | $CH_3$ | O | |
| 1.327 | 2-Methoxypyridin-4-yl | 1,2,8 | $CH_3$ | $CH_3$ | O | |
| 1.328 | 3-Methoxypyridin-4-yl | 1,2,8 | $CH_3$ | $CH_3$ | O | |
| 1.329 | 2-Ethoxypyridin-4-yl | 1,2,8 | $CH_3$ | $CH_3$ | O | |
| 1.330 | 3-Ethoxypyridin-4-yl | 1,2,8 | $CH_3$ | $CH_3$ | O | |
| 1.331 | 2-Propoxypyridin-4-yl | 1,2,8 | $CH_3$ | $CH_3$ | O | |
| 1.332 | 3-Propoxypyridin-4-yl | 1,2,8 | $CH_3$ | $CH_3$ | O | |
| 1.333 | 2-Isopropoxypyridin-4-yl | 1,2,8 | $CH_3$ | $CH_3$ | O | |
| 1.334 | 3-Isopropoxypyridin-4-yl | 1,2,8 | $CH_3$ | $CH_3$ | O | |
| 1.335 | 2-(2,2,2-Trifluoroethoxy)pyridin-4-yl | 1,2,8 | $CH_3$ | $CH_3$ | O | |
| 1.336 | 3-(2,2,2-Trifluoroethoxy)pyridin-4-yl | 1,2,8 | $CH_3$ | $CH_3$ | O | |
| 1.337 | 2-Methylthiopyridin-4-yl | 1,2,8 | $CH_3$ | $CH_3$ | O | |
| 1.338 | 3-Methylthiopyridin-4-yl | 1,2,8 | $CH_3$ | $CH_3$ | O | |
| 1.339 | 2-Trifluoromethylpyridin-4-yl | 1,2,8 | $CH_3$ | $CH_3$ | O | |
| 1.340 | 3-Trifluoromethylpyridin-4-yl | 1,2,8 | $CH_3$ | $CH_3$ | O | |
| 1.341 | 2-Fluoropyridin-4-yl | 1,2,8 | $CH_3$ | $CH_3$ | O | |
| 1.342 | 3-Fluoropyridin-4-yl | 1,2,8 | $CH_3$ | $CH_3$ | O | |
| 1.343 | 1-Methyl-5-methylthio-1,2,4-triazol-3-yl | 1,2,8 | $CH_3$ | $CH_3$ | O | |
| 1.344 | 2-Trifluoromethoxypyridin-4-yl | 1,2,8 | $CH_3$ | $CH_3$ | O | |
| 1.345 | 3-Trifluoromethoxypyridin-4-yl | 1,2,8 | $CH_3$ | $CH_3$ | O | |
| 1.346 | 2-(2,2,2-Trifluoroethoxy)pyridin-5-yl | 1,2,8 | $CH_3$ | $CH_3$ | O | |
| 1.347 | 2-Dimethylaminoxypyridin-5-yl | 1,2,8 | $CH_3$ | $CH_3$ | O | |

TABLE 1-continued

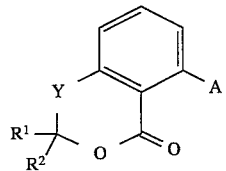

| No. | A | Method | R¹ | R² | Y | Physical data |
|---|---|---|---|---|---|---|
| 1.348 | 2-Cyclopentyloxypyridin-5-yl | 1,2,8 | CH₃ | CH₃ | O | |
| 1.349 | 2-Methylpyridin-3-yl | 1,2,8 | CH₃ | CH₃ | O | |
| 1.350 | 4-Methylpyridin-3-yl | 1,2,8 | CH₃ | CH₃ | O | |
| 1.351 | 3-Methylpyridin-5-yl | 1,2,8 | CH₃ | CH₃ | O | |
| 1.352 | 2-Methylpyridin-5-yl | 1,2,8 | CH₃ | CH₃ | O | |
| 1.353 | 2,4-Dimethylpyridin-3-yl | 1,2,8 | CH₃ | CH₃ | O | |
| 1.354 | 2,6-Dimethylpyridin-3-yl | 1,2,8 | CH₃ | CH₃ | O | |
| 1.355 | 2,3-Dimethylpyridin-5-yl | 1,2,8 | CH₃ | CH₃ | O | |
| 1.356 | 2,4-Dimethylpyridin-5-yl | 1,2,8 | CH₃ | CH₃ | O | |
| 1.357 | 2-Methoxypyridin-3-yl | 1,2,8 | CH₃ | CH₃ | O | M.p. = 148–150° C. |
| 1.358 | 4-Methoxypyridin-3-yl | 1,2,8 | CH₃ | CH₃ | O | |
| 1.359 | 3-Methoxypyridin-5-yl | 1,2,8 | CH₃ | CH₃ | O | M.p. = 181–182° C. |
| 1.360 | 2-Ethoxypyridin-3-yl | 1,2,8 | CH₃ | CH₃ | O | M.p. = 139–140° C. |
| 1.361 | 4-Ethoxypyridin-3-yl | 1,2,8 | CH₃ | CH₃ | O | |
| 1.362 | 3-Ethoxypyridin-5-yl | 1,2,8 | CH₃ | CH₃ | O | M.p. = 136–137° C. |
| 1.363 | 2-Propoxypyridin-3-yl | 1,2,8 | CH₃ | CH₃ | O | |
| 1.364 | 4-Propoxypyridin-3-yl | 1,2,8 | CH₃ | CH₃ | O | |
| 1.365 | 3-Propoxypyridin-5-yl | 1,2,8 | CH₃ | CH₃ | O | |
| 1.366 | 2-Propoxypyridin-5-yl | 1,2,8 | CH₃ | CH₃ | O | |
| 1.367 | 2-Isopropoxypyridin-3-yl | 1,2,8 | CH₃ | CH₃ | O | |
| 1.368 | 4-Isopropoxypyridin-3-yl | 1,2,8 | CH₃ | CH₃ | O | |
| 1.369 | 3-Isopropoxypyridin-5-yl | 1,2,8 | CH₃ | CH₃ | O | M.p. = 105–107° C. |
| 1.370 | 2-Methylthiopyridin-3-yl | 1,2,8 | CH₃ | CH₃ | O | M.p. = 192–193° C. |
| 1.371 | 4-Methylthiopyridin-3-yl | 1,2,8 | CH₃ | CH₃ | O | |
| 1.372 | 3-Methylthiopyridin-5-yl | 1,2,8 | CH₃ | CH₃ | O | M.p. = 151° C. |
| 1.373 | 2-(2,2,2-Trifluoroethoxy)pyridin-3-yl | 1,2,8 | CH₃ | CH₃ | O | |
| 1.374 | 4-(2,2,2-Trifluoroethoxy)pyridin-3-yl | 1,2,8 | CH₃ | CH₃ | O | |
| 1.375 | 3-(2,2,2-Trifluoroethoxy)pyridin-5-yl | 1,2,8 | CH₃ | CH₃ | O | |
| 1.376 | 2-(2,2,2-Trifluoroethoxy)pyridin-5-yl | 1,2,8 | CH₃ | CH₃ | O | |
| 1.377 | 2-Trifluoromethylpyridin-3-yl | 1,2,8 | CH₃ | CH₃ | O | |
| 1.378 | 4-Trifluoromethylpyridin-3-yl | 1,2,8 | CH₃ | CH₃ | O | |
| 1.379 | 3-Trifluoromethylpyridin-5-yl | 1,2,8 | CH₃ | CH₃ | O | |
| 1.380 | 2-Trifluoromethylpyridin-5-yl | 1,2,8 | CH₃ | CH₃ | O | |
| 1.381 | 2-Fluoropyridin-3-yl | 1,2,8 | CH₃ | CH₃ | O | |
| 1.382 | 4-Fluoropyridin-3-yl | 1,2,8 | CH₃ | CH₃ | O | |
| 1.383 | 3-Fluoropyridin-5-yl | 1,2,8 | CH₃ | CH₃ | O | |
| 1.384 | 2-Fluoropyridin-5-yl | 1,2,8 | CH₃ | CH₃ | O | |
| 1.385 | 2-Trifluoromethoxypyridin-3-yl | 1,2,8 | CH₃ | CH₃ | O | |
| 1.386 | 4-Trifluoromethoxypyridin-3-yl | 1,2,8 | CH₃ | CH₃ | O | |
| 1.387 | 3-Trifluoromethoxypyridin-5-yl | 1,2,8 | CH₃ | CH₃ | O | |
| 1.388 | 2-Trifluoromethoxypyridin-5-yl | 1,2,8 | CH₃ | CH₃ | O | |
| 1.389 | 3-(2,2,2-Trifluoroethoxy)pyridin-5-yl | 1,2,8 | CH₃ | CH₃ | O | |
| 1.390 | 3-Dimethylaminoxypyridin-5-yl | 1,2,8 | CH₃ | CH₃ | O | |
| 1.391 | 2-(2,2,2-Trifluoroethoxy)pyridin-3-yl | 1,2,8 | CH₃ | CH₃ | O | |
| 1.392 | 2-Dimethylaminoxypyridin-3-yl | 1,2,8 | CH₃ | CH₃ | O | |
| 1.393 | 4-(2,2,2-Trifluoroethoxy)pyridin-3-yl | 1,2,8 | CH₃ | CH₃ | O | |
| 1.394 | 4-Dimethylaminoxypyridin-3-yl | 1,2,8 | CH₃ | CH₃ | O | |
| 1.395 | 3-(2,2,2-Trifluoro- | 1,2,8 | CH₃ | CH₃ | O | |

TABLE 1-continued

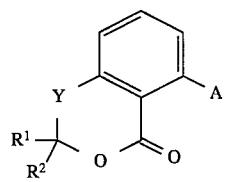

| No. | A | Method | R¹ | R² | Y | Physical data |
|---|---|---|---|---|---|---|
| | ethoxy)pyridin-2-yl | | | | | |
| 1.396 | 4-(2,2,2-Trifluoro-ethoxy)pyridin-2-yl | 1,2,8 | $CH_3$ | $CH_3$ | O | |
| 1.397 | 5-(2,2,2-Trifluoro-ethoxy)pyridin-2-yl | 1,2,8 | $CH_3$ | $CH_3$ | O | |
| 1.398 | 6-(2,2,2-Trifluoro-ethoxy)pyridin-2-yl | 1,2,8 | $CH_3$ | $CH_3$ | O | M.p. = 143–144° C. |
| 1.399 | 6-Cyclopentyloxypyridin-2-yl | 1,2,8 | $CH_3$ | $CH_3$ | O | M.p. = 140–142° C. |
| 1.400 | 3-Methylpyridin-2-yl | 1,2,8 | $CH_3$ | $CH_3$ | O | |
| 1.401 | 4-Methylpyridin-2-yl | 1,2,8 | $CH_3$ | $CH_3$ | O | |
| 1.402 | 3,4-Dimethylpyridin-2-yl | 1,2,8 | $CH_3$ | $CH_3$ | O | |
| 1.403 | 3,5-Dimethylpyridin-2-yl | 1,2,8 | $CH_3$ | $CH_3$ | O | |
| 1.404 | 3,6-Dimethylpyridin-2-yl | 1,2,8 | $CH_3$ | $CH_3$ | O | |
| 1.405 | 4,5-Dimethylpyridin-2-yl | 1,2,8 | $CH_3$ | $CH_3$ | O | |
| 1.406 | 5,6-Dimethylpyridin-2-yl | 1,2,8 | $CH_3$ | $CH_3$ | O | |
| 1.407 | 3-Methoxypyridin-2-yl | 1,2,8 | $CH_3$ | $CH_3$ | O | |
| 1.408 | 4-Methoxypyridin-2-yl | 1,2,8 | $CH_3$ | $CH_3$ | O | |
| 1.409 | 5-Methoxypyridin-2-yl | 1,2,8 | $CH_3$ | $CH_3$ | O | |
| 1.410 | 3-Ethoxypyridin-2-yl | 1,2,8 | $CH_3$ | $CH_3$ | O | |
| 1.411 | 4-Ethoxypyridin-2-yl | 1,2,8 | $CH_3$ | $CH_3$ | O | |
| 1.412 | 5-Ethoxypyridin-2-yl | 1,2,8 | $CH_3$ | $CH_3$ | O | |
| 1.413 | 3-Propoxypyridin-2-yl | 1,2,8 | $CH_3$ | $CH_3$ | O | |
| 1.414 | 4-Propoxypyridin-2-yl | 1,2,8 | $CH_3$ | $CH_3$ | O | |
| 1.415 | 5-Propoxypyridin-2-yl | 1,2,8 | $CH_3$ | $CH_3$ | O | |
| 1.416 | 6-Propoxypyridin-2-yl | 1,2,8 | $CH_3$ | $CH_3$ | O | M.p. = 84–86° C. |
| 1.417 | 3-Isopropoxypyridin-2-yl | 1,2,8 | $CH_3$ | $CH_3$ | O | |
| 1.418 | 4-Isopropoxypyridin-2-yl | 1,2,8 | $CH_3$ | $CH_3$ | O | |
| 1.419 | 5-Isopropoxypyridin-2-yl | 1,2,8 | $CH_3$ | $CH_3$ | O | |
| 1.420 | 3-Methylthiopyridin-2-yl | 1,2,8 | $CH_3$ | $CH_3$ | O | |
| 1.421 | 4-Methylthiopyridin-2-yl | 1,2,8 | $CH_3$ | $CH_3$ | O | |
| 1.422 | 5-Methylthiopyridin-2-yl | 1,2,8 | $CH_3$ | $CH_3$ | O | |
| 1.423 | 3-Ethylthiopyridin-2-yl | 1,2,8 | $CH_3$ | $CH_3$ | O | |
| 1.424 | 4-Ethylthiopyridin-2-yl | 1,2,8 | $CH_3$ | $CH_3$ | O | |
| 1.425 | 5-Ethylthiopyridin-2-yl | 1,2,8 | $CH_3$ | $CH_3$ | O | |
| 1.426 | 6-Ethylthiopyridin-2-yl | 1,2,8 | $CH_3$ | $CH_3$ | O | |
| 1.427 | 3-Trifluoromethylpyridin-2-yl | 1,2,8 | $CH_3$ | $CH_3$ | O | |
| 1.428 | 4-Trifluoromethylpyridin-2-yl | 1,2,8 | $CH_3$ | $CH_3$ | O | |
| 1.429 | 5-Trifluoromethylpyridin-2-yl | 1,2,8 | $CH_3$ | $CH_3$ | O | |
| 1.430 | 6-Trifluoromethylpyridin-2-yl | 1,2,8 | $CH_3$ | $CH_3$ | O | |
| 1.431 | 3-Fluoropyridin-2-yl | 1,2,8 | $CH_3$ | $CH_3$ | O | |
| 1.432 | 4-Fluoropyridin-2-yl | 1,2,8 | $CH_3$ | $CH_3$ | O | |
| 1.433 | 5-Fluoropyridin-2-yl | 1,2,8 | $CH_3$ | $CH_3$ | O | |
| 1.434 | 6-Fluoropyridin-2-yl | 1,2,8 | $CH_3$ | $CH_3$ | O | |
| 1.435 | 3-Trifluoromethoxypyridin-2-yl | 1,2,8 | $CH_3$ | $CH_3$ | O | |
| 1.436 | 4-Trifluoromethoxypyridin-2-yl | 1,2,8 | $CH_3$ | $CH_3$ | O | |
| 1.437 | 5-Trifluoromethoxypyridin-2-yl | 1,2,8 | $CH_3$ | $CH_3$ | O | |
| 1.438 | 6-Trifluoromethoxypyridin-2-yl | 1,2,8 | $CH_3$ | $CH_3$ | O | |
| 1.439 | 4-Dimethylaminoxypyridin-2-yl | 1,2,8 | $CH_3$ | $CH_3$ | O | |
| 1.440 | 3-Dimethylaminoxypyridin-2-yl | 1,2,8 | $CH_3$ | $CH_3$ | O | |
| 1.441 | 5-Dimethylaminoxypyridin-2-yl | 1,2,8 | $CH_3$ | $CH_3$ | O | |
| 1.442 | 6-Dimethylaminoxypyridin-2-yl | 1,2,8 | $CH_3$ | $CH_3$ | O | |
| 1.443 | Pyrimidin-2-yl | 1,2,8 | $CH_3$ | $CH_3$ | O | |
| 1.444 | Pyrimidin-4-yl | 1,2,8 | $CH_3$ | $CH_3$ | O | |
| 1.445 | Pyrimidin-5-yl | 1,2,8 | $CH_3$ | $CH_3$ | O | M.p. = 176–177° C. |

TABLE 1-continued

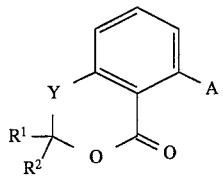

| No. | A | Method | R¹ | R² | Y | Physical data |
|---|---|---|---|---|---|---|
| 1.446 | 4-Methoxypyrimidin-2-yl | 1,2,8 | CH₃ | CH₃ | O | |
| 1.447 | 5-Methoxypyrimidin-2-yl | 1,2,8 | CH₃ | CH₃ | O | |
| 1.448 | 4,6-Dimethoxy-pyrimidin-2-yl | 1,2,8 | CH₃ | CH₃ | O | |
| 1.449 | 2-Methoxypyrimidin-4-yl | 1,2,8 | CH₃ | CH₃ | O | |
| 1.450 | 6-Methoxypyrimidin-4-yl | 1,2,8 | CH₃ | CH₃ | O | |
| 1.451 | 2,6-Dimethoxy-pyrimidin-4-yl | 1,2,8 | CH₃ | CH₃ | O | |
| 1.452 | 2-Methoxypyrimidin-5-yl | 1,2,8 | CH₃ | CH₃ | O | |
| 1.453 | 4-Methoxypyrimidin-5-yl | 1,2,8 | CH₃ | CH₃ | O | |
| 1.454 | 2,4-Dimethoxy-pyrimidin-5-yl | 1,2,8 | CH₃ | CH₃ | O | |
| 1.455 | 4-Methylthiopyrimidin-2-yl | 1,2,8 | CH₃ | CH₃ | O | |
| 1.456 | 2-(2,2,2-Trifluoro-ethoxy)pyrimidin-4-yl | 1,2,8 | CH₃ | CH₃ | O | |
| 1.457 | 2-(2-Dimethylamino-ethoxy)pyridin-5-yl | 1,2,8 | CH₃ | CH₃ | O | M.p. = 112° C. |
| 1.458 | 2-(2-Methoxyethoxy)-pyridin-5-yl | 1,2,8 | CH₃ | CH₃ | O | M.p. = 161° C. |
| 1.459 | 6-(2-Methoxyethyl)-pyridin-2-yl | 1,2,8 | CH₃ | CH₃ | O | |
| 1.460 | 2-(Methoxymethoxy)-pyridin-5-yl | 1,2,8 | CH₃ | CH₃ | O | |
| 1.461 | 6-(Methoxymethoxy)-pyridin-2-yl | 1,2,8 | CH₃ | CH₃ | O | |
| 1.462 | 2-(Methoxymethyl)-pyridin-5-yl | 1,2,8 | CH₃ | CH₃ | O | |
| 1.463 | 6-(Methoxymethyl)-pyridin-2-yl | 1,2,8 | CH₃ | CH₃ | O | |
| 1.464 | 6-(Methylthiomethyl)-pyridin-2-yl | 1,2,8 | CH₃ | CH₃ | O | |
| 1.465 | 1-Naphthyl | 1,2,8 | CH₃ | CH₃ | O | |
| 1.466 | 2-Naphthyl | 1,2,8 | CH₃ | CH₃ | O | |
| 1.467 | 5-Benzotriazolyl | 1,2,8 | CH₃ | CH₃ | O | |
| 1.468 | 2-Benzothiazolyl | 1,2,8 | CH₃ | CH₃ | O | |
| 1.469 | 2-Benzoxazolyl | 1,2,8 | CH₃ | CH₃ | O | |
| 1.470 | Quinolin-2-yl | 1,2,8 | CH₃ | CH₃ | O | |
| 1.471 | Quinolin-4-yl | 1,2,8 | CH₃ | CH₃ | O | |
| 1.472 | Benzothien-2-yl | 1,2,8 | CH₃ | CH₃ | O | |
| 1.473 | 2,3-Dihydrofuran-4-yl | 1,2,8 | CH₃ | CH₃ | O | |
| 1.474 | 1-Cyclopentadienyl | 1,2,8 | CH₃ | CH₃ | O | |
| 1.475 | 5-Cyclopentadienyl | 1,2,8 | CH₃ | CH₃ | O | |
| 1.476 | Vinyl | 1,2,8, 1a,7 | CH₃ | CH₃ | O | |
| 1.477 | 1-Chlorovinyl | 1,2,8, 1a,7 | CH₃ | CH₃ | O | |
| 1.478 | 2-Chlorovinyl | 1,2,8, 1a,7 | CH₃ | CH₃ | O | |
| 1.479 | 2-Propenyl | 1a,7 | CH₃ | CH₃ | O | |
| 1.480 | 1-Propenyl | 1,2,8, 1a,7 | CH₃ | CH₃ | O | |
| 1.481 | 2-Methylpropen-1-yl | 1,2,8, 1a,7 | CH₃ | CH₃ | O | |
| 1.482 | 1-Propynyl | 5 | CH₃ | CH₃ | O | |
| 1.483 | Tetrahydropyran-4-yl | 1,2,8, 1a,7 | CH₃ | CH₃ | O | |
| 1.484 | Tetrahydropyran-3-yl | 1,2,8, 1a,7 | CH₃ | CH₃ | O | |
| 1.485 | Tetrahydrothiopyran-3-yl | 1,2,8, 1a,7 | CH₃ | CH₃ | O | |
| 1.486 | Tetrahydrothiopyran-4-yl | 1,2,8, 1a,7 | CH₃ | CH₃ | O | |
| 1.487 | N-Methylpiperidin-4-yl | 1,2,8, 1a,7 | CH₃ | CH₃ | O | |
| 1.488 | N-Methylpyrrolidin-2-yl | 1,2,8, 1a,7 | CH₃ | CH₃ | O | |

TABLE 1-continued

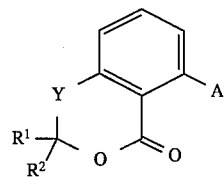

| No. | A | Method | R¹ | R² | Y | Physical data |
|---|---|---|---|---|---|---|
| 1.489 | Tetrahydrofuran-2-yl | 1,2,8, 1a,7 | CH₃ | CH₃ | O | |
| 1.490 | Tetrahydrofuran-3-yl | 1,2,8, 1a,7 | CH₃ | CH₃ | O | |
| 1.491 | 2-Allyloxy-pyridin-5-yl | 1,2,8 | CH₃ | CH₃ | O | |
| 1.492 | 6-Allyloxy-pyridin-2-yl | 1,2,8 | CH₃ | CH₃ | O | |
| 1.493 | 2-Methoxyphenyl | 1,2,8 | CH₃ | CH₃ | O | |
| 1.494 | 3-Methoxyphenyl | 1,2,8 | CH₃ | CH₃ | O | |
| 1.495 | 4-Methoxyphenyl | 1,2,8 | CH₃ | CH₃ | O | |
| 1.496 | 2-Ethoxyphenyl | 1,2,8 | CH₃ | CH₃ | O | |
| 1.497 | 3-Ethoxyphenyl | 1,2,8 | CH₃ | CH₃ | O | |
| 1.498 | 4-Ethoxyphenyl | 1,2,8 | CH₃ | CH₃ | O | |
| 1.499 | 2-Propoxyphenyl | 1,2,8 | CH₃ | CH₃ | O | |
| 1.500 | 3-Propoxyphenyl | 1,2,8 | CH₃ | CH₃ | O | |
| 1.501 | 4-Propoxyphenyl | 1,2,8 | CH₃ | CH₃ | O | |
| 1.502 | 2-Isopropyloxyphenyl | 1,2,8 | CH₃ | CH₃ | O | |
| 1.503 | 3-Isopropyloxyphenyl | 1,2,8 | CH₃ | CH₃ | O | |
| 1.504 | 4-Isopropyloxyphenyl | 1,2,8 | CH₃ | CH₃ | O | |
| 1.505 | 4-(2,2,2-Trifluoro-ethoxy)phenyl | 1,2,8 | CH₃ | CH₃ | O | |
| 1.506 | 3-(2,2,2-Trifluoro-ethoxy)phenyl | 1,2,8 | CH₃ | CH₃ | O | |
| 1.507 | 2-(2,2,2-Trifluoro-ethoxy)phenyl | 1,2,8 | CH₃ | CH₃ | O | |
| 1.508 | 4-Cyclopropyloxyphenyl | 1,2,8 | CH₃ | CH₃ | O | |
| 1.509 | 4-(Trifluoro-methoxy)phenyl | 1,2,8 | CH₃ | CH₃ | O | |
| 1.510 | 4-(Difluoro-methoxy)phenyl | 1,2,8 | CH₃ | CH₃ | O | |
| 1.511 | 4-(Difluorochloro-methoxy)phenyl | 1,2,8 | CH₃ | CH₃ | O | |
| 1.512 | 4-(Methoxymethoxy)phenyl | 1,2,8 | CH₃ | CH₃ | O | |
| 1.513 | 4-(2-Methoxy-athoxy)phenyl | 1,2,8 | CH₃ | CH₃ | O | |
| 1.514 | 4-(Ethoxymethoxy)phenyl | 1,2,8 | CH₃ | CH₃ | O | |
| 1.515 | 4-(Ethoxymethyl)phenyl | 1,2,8 | CH₃ | CH₃ | O | |
| 1.516 | 4-(Methylthio)phenyl | 1,2,8 | CH₃ | CH₃ | O | |
| 1.517 | 4-(Methylthio-methyl)phenyl | 1,2,8 | CH₃ | CH₃ | O | |
| 1.518 | 4-(2-Dimethylamino-ethoxy)phenyl | 1,2,8 | CH₃ | CH₃ | O | |
| 1.519 | 4-(2-Propenyl)phenyl | 1,2,8 | CH₃ | CH₃ | O | |
| 1.520 | 4-(Vinyloxy)phenyl | 1,2,8 | CH₃ | CH₃ | O | |
| 1.521 | 4-(Allyloxy)phenyl | 1,2,8 | CH₃ | CH₃ | O | |
| 1.522 | 4-Fluorophenyl | 1,2,8 | CH₃ | CH₃ | O | |
| 1.523 | Cyclopenten-3-yl | 1,2,8 | CH₃ | CH₃ | O | |
| 1.524 | Cyclopenten-1-yl | 1,2,8 | CH₃ | CH₃ | O | |
| 1.525 | Cyclohexen-1-yl | 1,2,8 | CH₃ | CH₃ | O | |
| 1.526 | Cyclohexen-3-yl | 1,2,8 | CH₃ | CH₃ | O | |
| 1.527 | Fluorosulfonyloxy | 1b | CH₃ | CH₃ | O | |
| 1.528 | Chlorine | 1a,7 | CH₃ | CH₃ | O | |
| 1.529 | Iodine | 1a,7 | CH₃ | CH₃ | O | |
| 1.530 | Fluorine | 1a,7 | CH₃ | CH₃ | O | |
| 1.531 | Cyano | 1a,7 | CH₃ | CH₃ | O | |
| 1.532 | Nitro | 1a,7 | CH₃ | CH₃ | O | |
| 1.533 | Formyl | 1a,7 | CH₃ | CH₃ | O | |
| 1.534 | 6-Dimethylamino-pyridin-2-yl | 1,2,8 | CH₃ | CH₃ | O | |
| 1.535 | 2-Dimethylamino-pyridin-5-yl | 1,2,8 | CH₃ | CH₃ | O | |
| 1.536 | 4-Dimethylaminophenyl | 1,2,8 | CH₃ | CH₃ | O | |
| 1.537 | 2-Dimethylamino-pyridin-3-yl | 1,2,8 | CH₃ | CH₃ | O | |
| 1.538 | 2-(2-Propanimin-oxy)pyridin-5-yl | 1,2,8 | CH₃ | CH₃ | O | |
| 1.539 | 6-(2-Propanimin-oxy)pyridin-2-yl | 1,2,8 | CH₃ | CH₃ | O | |

TABLE 1-continued

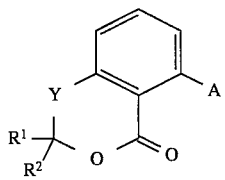

| No. | A | Method | R¹ | R² | Y | Physical data |
|---|---|---|---|---|---|---|
| 1.540 | 2-(2-Propanimin-oxy)pyridin-3-yl | 1,2,8 | CH₃ | CH₃ | O | |
| 1.541 | Ethyl | 1a,7 | CH₃ | CH₃ | O | |
| 1.542 | Propyl | 1a,7 | CH₃ | CH₃ | O | |
| 1.543 | Methoxymethyl | 1a,7 | CH₃ | CH₃ | O | |
| 1.544 | 2-Methoxyethyl | 1a,7 | CH₃ | CH₃ | O | |
| 1.545 | 1-Chloroethyl | 1a,7 | CH₃ | CH₃ | O | |
| 1.546 | 2,2,2-Trifluoroethyl | 1a,7 | CH₃ | CH₃ | O | |
| 1.547 | Methylthiomethyl | 1a,7 | CH₃ | CH₃ | O | |
| 1.548 | 3-(2-Propanimin-oxy)propenyl | 1,2,8, 1a,7 | CH₃ | CH₃ | O | |
| 1.549 | (2-Propaniminoxy)methyl | 1a,7 | CH₃ | CH₃ | O | |
| 1.550 | 6-(2-Methoxyethoxy)-pyridin-2-yl | 1,2,8 | CH₃ | CH₃ | O | δ (C): 1.80 (s); 3.46 (s); 3.75 (t); 4.50 (t); 6.81 (d); 7.03 (m); 7.20 (d); 7.50–7,70 (m). |
| 1.551 | 2-Methoxy-3-methyl-pyridin-5-yl | 1,2,8 | CH₃ | CH₃ | O | M.p. = 166–168° C. |
| 1.552 | 2-Dimethylamino-pyridin-5-yl | 1,2,8 | CH₃ | CH₃ | O | |
| 1.553 | 2-Dimethylamino-pyridin-6-yl | 1,2,8 | CH₃ | CH₃ | O | |
| 1.554 | 5-Dimethylamino-pyridin-2-yl | 1,2,8 | CH₃ | CH₃ | O | |
| 1.555 | 2-Chloropyridin-4-yl | 10 | CH₃ | CH₃ | O | |

δ (C): ¹H-NMR in CDCl₃, data in [ppm]
δ (D): ¹H-NMR in [D₆]-dimethyl sulfoxide, data in [ppm]

TABLE 2

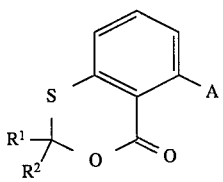

| No. | A | R¹ | R² | Physical data |
|---|---|---|---|---|
| 2.001 | Trimethylsilylethynyl | CH₃ | CH₃ | |
| 2.002 | 3,3-Dimethyl-1-butynyl | CH₃ | CH₃ | |
| 2.003 | Phenylethynyl | CH₃ | CH₃ | |
| 2.004 | 3-Methoxy-1-propynyl | CH₃ | CH₃ | |
| 2.005 | 3-(Dimethylamino)-1-propynyl | CH₃ | CH₃ | |
| 2.006 | 1-Pentynyl | CH₃ | CH₃ | |
| 2.007 | Pyridin-2-yl | CH₃ | CH₃ | |
| 2.008 | Cyclohexylethynyl | CH₃ | CH₃ | |
| 2.009 | 3-Methyl-3-buten-1-ynyl | CH₃ | CH₃ | |
| 2.010 | Pyridin-4-yl | CH₃ | CH₃ | |
| 2.011 | 4-Methyloxazol-2-yl | CH₃ | CH₃ | |
| 2.012 | Pyridin-3-yl | CH₃ | CH₃ | |
| 2.013 | 5-Methyloxazol-2-yl | CH₃ | CH₃ | |
| 2.014 | 3-(2-Propaniminoxy)-1-propynyl | CH₃ | CH₃ | |
| 2.015 | 3-(Morpholin-4-yl)-1-propynyl | CH₃ | CH₃ | |
| 2.016 | 4-(1,3-Dioxolan-2-yl)-3-methyl- | CH₃ | CH₃ | |

TABLE 2-continued

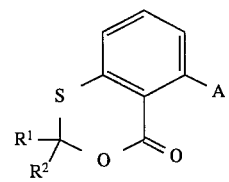

| No. | A | R¹ | R² | Physical data |
|---|---|---|---|---|
| | 3-buten-1-ynyl | | | |
| 2.017 | Ethynyl | CH₃ | CH₃ | |
| 2.018 | 6-Methylpyridin-2-yl | CH₃ | CH₃ | |
| 2.019 | 5-Methylpyridin-2-yl | CH₃ | CH₃ | |
| 2.020 | 3-Methylisoxazol-5-yl | CH₃ | CH₃ | |
| 2.021 | 1-Methylpyrrol-2-yl | CH₃ | CH₃ | |
| 2.022 | 3-Ethylisoxazol-5-yl | CH₃ | CH₃ | |
| 2.023 | 2-Methoxypyridin-5-yl | CH₃ | CH₃ | |
| 2.024 | 2-Isopropoxypyridin-5-yl | CH₃ | CH₃ | |
| 2.025 | 2-Ethylthiopyridin-5-yl | CH₃ | CH₃ | |
| 2.026 | 2-Methylthiopyridin-5-yl | CH₃ | CH₃ | |
| 2.027 | 2-Ethoxypyridin-5-yl | CH₃ | CH₃ | |
| 2.028 | 3-Isopropylisoxazol-5-yl | CH₃ | CH₃ | |
| 2.029 | 2-Cyclopropylpyridin-4-yl | CH₃ | CH₃ | |
| 2.030 | 2-Cyclopropylpyridin-5-yl | CH₃ | CH₃ | |
| 2.031 | 2-Isopropylthiopyridin-5-yl | CH₃ | CH₃ | |
| 2.032 | Thiazol-4-yl | CH₃ | CH₃ | |

TABLE 2-continued

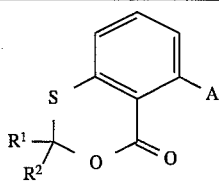

| No. | A | R$^1$ | R$^2$ | Physical data |
|---|---|---|---|---|
| 2.033 | Thiazol-5-yl | CH$_3$ | CH$_3$ | |
| 2.034 | Oxazol-2-yl | CH$_3$ | CH$_3$ | |
| 2.035 | Methyl | H | t-C$_4$H$_9$ | |
| 2.036 | Methyl | H | C$_6$H$_5$ | |
| 2.037 | Bromine | CH$_3$ | CH$_3$ | |
| 2.038 | Cyclopropyl | CH$_3$ | CH$_3$ | |
| 2.039 | Phenyl | CH$_3$ | CH$_3$ | |
| 2.040 | 3,4-(Ethylenedioxy)phenyl | CH$_3$ | CH$_3$ | |
| 2.041 | 4-Formylphenyl | CH$_3$ | CH$_3$ | |
| 2.042 | 6-Methoxypyridin-2-yl | CH$_3$ | CH$_3$ | M.p. = 110–112° C. |
| 2.043 | 6-Methylthiopyridin-2-yl | CH$_3$ | CH$_3$ | |
| 2.044 | 6-Isopropoxypyridin-2-yl | CH$_3$ | CH$_3$ | |
| 2.045 | 6-Ethoxypyridin-2-yl | CH$_3$ | CH$_3$ | |
| 2.046 | 4-Methylpyridin-2-yl | CH$_3$ | CH$_3$ | |
| 2.047 | 6-Isopropylthiopyridin-2-yl | CH$_3$ | CH$_3$ | |
| 2.048 | 4,6-Dimethylpyridin-2-yl | CH$_3$ | CH$_3$ | |
| 2.049 | 3,5-Dimethylisoxazol-4-yl | CH$_3$ | CH$_3$ | |
| 2.050 | 6-(2-Dimethylaminoethoxy)pyridin-2-yl | CH$_3$ | CH$_3$ | |
| 2.051 | 3-Furyl | CH$_3$ | CH$_3$ | |
| 2.052 | 2-Furyl | CH$_3$ | CH$_3$ | |
| 2.053 | 2-Methyl-3-furyl | CH$_3$ | CH$_3$ | |
| 2.054 | 4-Methyl-3-furyl | CH$_3$ | CH$_3$ | |
| 2.055 | 3-Methyl-2-furyl | CH$_3$ | CH$_3$ | |
| 2.056 | 4-Methyl-2-furyl | CH$_3$ | CH$_3$ | |
| 2.057 | 5-Methyl-2-furyl | CH$_3$ | CH$_3$ | |
| 2.058 | 5-Methoxy-2-furyl | CH$_3$ | CH$_3$ | |
| 2.059 | 2-Thienyl | CH$_3$ | CH$_3$ | |
| 2.060 | 3-Thienyl | CH$_3$ | CH$_3$ | |
| 2.061 | 5-Methoxy-2-thienyl | CH$_3$ | CH$_3$ | |
| 2.062 | 4-Methoxy-2-thienyl | CH$_3$ | CH$_3$ | |
| 2.063 | 3-Methoxy-2-thienyl | CH$_3$ | CH$_3$ | |
| 2.064 | 5-Fluoro-2-thienyl | CH$_3$ | CH$_3$ | |
| 2.065 | 3-Fluoro-2-thienyl | CH$_3$ | CH$_3$ | |
| 2.066 | 4-Fluoro-2-thienyl | CH$_3$ | CH$_3$ | |
| 2.067 | 5-Methyl-2-thienyl | CH$_3$ | CH$_3$ | |
| 2.068 | 3-Methyl-2-thienyl | CH$_3$ | CH$_3$ | |
| 2.069 | 4-Methyl-2-thienyl | CH$_3$ | CH$_3$ | |
| 2.070 | 5-Methylthio-2-thienyl | CH$_3$ | CH$_3$ | |
| 2.071 | 3-Methylthio-2-thienyl | CH$_3$ | CH$_3$ | |
| 2.072 | 4-Methylthio-2-thienyl | CH$_3$ | CH$_3$ | |
| 2.073 | 5-Dimethylamino-2-thienyl | CH$_3$ | CH$_3$ | |
| 2.074 | 3-Dimethylamino-2-thienyl | CH$_3$ | CH$_3$ | |
| 2.075 | 4-Dimethylamino-2-thienyl | CH$_3$ | CH$_3$ | |
| 2.076 | 4,5-Dimethyl-2-thienyl | CH$_3$ | CH$_3$ | |
| 2.077 | 3,4-Dimethyl-2-thienyl | CH$_3$ | CH$_3$ | |
| 2.078 | 3,5-Dimethyl-2-thienyl | CH$_3$ | CH$_3$ | |
| 2.079 | 5-Methoxy-3-thienyl | CH$_3$ | CH$_3$ | |
| 2.080 | 4-Methoxy-3-thienyl | CH$_3$ | CH$_3$ | |
| 2.081 | 2-Methoxy-3-thienyl | CH$_3$ | CH$_3$ | |
| 2.082 | 5-Fluoro-3-thienyl | CH$_3$ | CH$_3$ | |
| 2.083 | 2-Fluoro-3-thienyl | CH$_3$ | CH$_3$ | |
| 2.084 | 4-Fluoro-3-thienyl | CH$_3$ | CH$_3$ | |
| 2.085 | 5-Methyl-3-thienyl | CH$_3$ | CH$_3$ | |
| 2.086 | 2-Methyl-3-thienyl | CH$_3$ | CH$_3$ | |
| 2.087 | 4-Methyl-3-thienyl | CH$_3$ | CH$_3$ | |
| 2.088 | 5-Methylthio-3-thienyl | CH$_3$ | CH$_3$ | |
| 2.089 | 2-Methylthio-3-thienyl | CH$_3$ | CH$_3$ | |
| 2.090 | 4-Methylthio-3-thienyl | CH$_3$ | CH$_3$ | |
| 2.091 | 5-Dimethylamino-3-thienyl | CH$_3$ | CH$_3$ | |
| 2.092 | 2-Dimethylamino-3-thienyl | CH$_3$ | CH$_3$ | |
| 2.093 | 4-Dimethylamino-3-thienyl | CH$_3$ | CH$_3$ | |
| 2.094 | 4,5-Dimethyl-3-thienyl | CH$_3$ | CH$_3$ | |
| 2.095 | 2,4-Dimethyl-3-thienyl | CH$_3$ | CH$_3$ | |
| 2.096 | 2,5-Dimethyl-3-thienyl | CH$_3$ | CH$_3$ | |
| 2.097 | Oxazol-4-yl | CH$_3$ | CH$_3$ | |

TABLE 2-continued

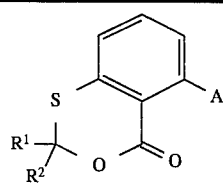

| No. | A | R$^1$ | R$^2$ | Physical data |
|---|---|---|---|---|
| 2.098 | Oxazol-5-yl | CH$_3$ | CH$_3$ | |
| 2.099 | 2-Methyloxazol-4-yl | CH$_3$ | CH$_3$ | |
| 2.100 | 2-Methyloxazol-5-yl | CH$_3$ | CH$_3$ | |
| 2.101 | 2-Ethyloxazol-4-yl | CH$_3$ | CH$_3$ | |
| 2.102 | 2-Ethyloxazol-5-yl | CH$_3$ | CH$_3$ | |
| 2.103 | 2-Methoxyoxazol-4-yl | CH$_3$ | CH$_3$ | |
| 2.104 | 2-Methoxyoxazol-5-yl | CH$_3$ | CH$_3$ | |
| 2.105 | 2-Methylthiooxazol-4-yl | CH$_3$ | CH$_3$ | |
| 2.106 | 2-Methylthiooxazol-5-yl | CH$_3$ | CH$_3$ | |
| 2.107 | 2-Ethoxyoxazol-4-yl | CH$_3$ | CH$_3$ | |
| 2.108 | 2-Ethoxyoxazol-5-yl | CH$_3$ | CH$_3$ | |
| 2.109 | 5-Methyloxazol-4-yl | CH$_3$ | CH$_3$ | |
| 2.110 | 4-Methyloxazol-5-yl | CH$_3$ | CH$_3$ | |
| 2.111 | 5-Methyloxazol-4-yl | CH$_3$ | CH$_3$ | |
| 2.112 | 4-Methyloxazol-5-yl | CH$_3$ | CH$_3$ | |
| 2.113 | Isoxazol-3-yl | CH$_3$ | CH$_3$ | |
| 2.114 | Isoxazol-4-yl | CH$_3$ | CH$_3$ | |
| 2.115 | Isoxazol-5-yl | CH$_3$ | CH$_3$ | |
| 2.116 | 4-Methylisoxazol-3-yl | CH$_3$ | CH$_3$ | |
| 2.117 | 5-Methylisoxazol-3-yl | CH$_3$ | CH$_3$ | |
| 2.118 | 3-Methylisoxazol-4-yl | CH$_3$ | CH$_3$ | |
| 2.119 | 5-Methylisoxazol-4-yl | CH$_3$ | CH$_3$ | |
| 2.120 | 4-Trifluoromethylisoxazol-3-yl | CH$_3$ | CH$_3$ | |
| 2.121 | 5-Trifluoromethylisoxazol-3-yl | CH$_3$ | CH$_3$ | |
| 2.122 | 3-Trifluoromethylisoxazol-4-yl | CH$_3$ | CH$_3$ | |
| 2.123 | 5-Trifluoromethylisoxazol-4-yl | CH$_3$ | CH$_3$ | |
| 2.124 | 3-Trifluoromethylisoxazol-5-yl | CH$_3$ | CH$_3$ | |
| 2.125 | 4-Trifluoromethylisoxazol-5-yl | CH$_3$ | CH$_3$ | |
| 2.126 | 1,2,3-Oxadiazol-4-yl | CH$_3$ | CH$_3$ | |
| 2.127 | 1,2,3-Oxadiazol-5-yl | CH$_3$ | CH$_3$ | |
| 2.128 | 5-Methyl-1,2,3-oxadiazol-4-yl | CH$_3$ | CH$_3$ | |
| 2.129 | 4-Methyl-1,2,3-oxadiazol-5-yl | CH$_3$ | CH$_3$ | |
| 2.130 | 5-Fluoro-1,2,3-oxadiazol-4-yl | CH$_3$ | CH$_3$ | |
| 2.131 | 4-Fluoro-1,2,3-oxadiazol-5-yl | CH$_3$ | CH$_3$ | |
| 2.132 | 5-Trifluoromethyl-1,2,3-oxadiazol-4-yl | CH$_3$ | CH$_3$ | |
| 2.133 | 4-Trifluoromethyl-1,2,3-oxadiazol-5-yl | CH$_3$ | CH$_3$ | |
| 2.134 | 1,3,4-Oxadiazol-2-yl | CH$_3$ | CH$_3$ | |
| 2.135 | 5-Methyl-1,3,4-oxadiazol-2-yl | CH$_3$ | CH$_3$ | |
| 2.136 | 5-Trifluoromethyl-1,3,4-oxadiazol-2-yl | CH$_3$ | CH$_3$ | |
| 2.137 | 5-Methylthio-1,3,4-oxadiazol-2-yl | CH$_3$ | CH$_3$ | |
| 2.138 | 1,2,4-Oxadiazol-3-yl | CH$_3$ | CH$_3$ | |
| 2.139 | 1,2,4-Oxadiazol-5-yl | CH$_3$ | CH$_3$ | |
| 2.140 | 5-Methyl-1,2,4-oxadiazol-3-yl | CH$_3$ | CH$_3$ | |
| 2.141 | 3-Methyl-1,2,4-oxadiazol-5-yl | CH$_3$ | CH$_3$ | |
| 2.142 | 5-Methoxy-1,2,4-oxadiazol-3-yl | CH$_3$ | CH$_3$ | |
| 2.143 | 3-Methoxy-1,2,4-oxadiazol-5-yl | CH$_3$ | CH$_3$ | |
| 2.144 | 5-Trifluoromethyl-1,2,4-oxadiazol-3-yl | CH$_3$ | CH$_3$ | |
| 2.145 | 3-Trifluoromethyl-1,2,4-oxadiazol-5-yl | CH$_3$ | CH$_3$ | |
| 2.146 | 1,2,5-Oxadiazol-3-yl | CH$_3$ | CH$_3$ | |
| 2.147 | 4-Methyl-1,2,5-oxadiazol-3-yl | CH$_3$ | CH$_3$ | |
| 2.148 | 4-Trifluoromethyl-1,2,5-oxadiazol-3-yl | CH$_3$ | CH$_3$ | |
| 2.149 | 1,2,3-Thiadiazol-4-yl | CH$_3$ | CH$_3$ | |
| 2.150 | 1,2,3-Thiadiazol-5-yl | CH$_3$ | CH$_3$ | |
| 2.151 | 5-Methyl-1,2,3-thiadiazol-4-yl | CH$_3$ | CH$_3$ | |
| 2.152 | 4-Methyl-1,2,3-thiadiazol-5-yl | CH$_3$ | CH$_3$ | |
| 2.153 | 5-Fluoro-1,2,3-thiadiazol-4-yl | CH$_3$ | CH$_3$ | |
| 2.154 | 4-Fluoro-1,2,3-thiadiazol-5-yl | CH$_3$ | CH$_3$ | |
| 2.155 | 5-Trifluoromethyl-1,2,3-thiadiazol-4-yl | CH$_3$ | CH$_3$ | |
| 2.156 | 4-Trifluoromethyl- | CH$_3$ | CH$_3$ | |

TABLE 2-continued

| No. | A | R¹ | R² | Physical data |
|---|---|---|---|---|
| | 1,2,3-thiadiazol-5-yl | | | |
| 2.157 | 1,3,4-Thiadiazol-2-yl | CH₃ | CH₃ | |
| 2.158 | 5-Methyl-1,3,4-thiadiazol-2-yl | CH₃ | CH₃ | |
| 2.159 | 5-Trifluoromethyl-1,3,4-thiadiazol-2-yl | CH₃ | CH₃ | |
| 2.160 | 5-Methylthio-1,3,4-thiadiazol-2-yl | CH₃ | CH₃ | |
| 2.161 | 1,2,4-Thiadiazol-3-yl | CH₃ | CH₃ | |
| 2.162 | 1,2,4-Thiadiazol-5-yl | CH₃ | CH₃ | |
| 2.163 | 5-Methyl-1,2,4-thiadiazol-3-yl | CH₃ | CH₃ | |
| 2.164 | 3-Methyl-1,2,4-thiadiazol-5-yl | CH₃ | CH₃ | |
| 2.165 | 5-Methoxy-1,2,4-thiadiazol-3-yl | CH₃ | CH₃ | |
| 2.166 | 3-Methoxy-1,2,4-thiadiazol-5-yl | CH₃ | CH₃ | |
| 2.167 | 5-Trifluoromethyl-1,2,4-thiadiazol-3-yl | CH₃ | CH₃ | |
| 2.168 | 3-Trifluoromethyl-1,2,4-thiadiazol-5-yl | CH₃ | CH₃ | |
| 2.169 | 1,2,5-Thiadiazol-3-yl | CH₃ | CH₃ | |
| 2.170 | 4-Methyl-1,2,5-thiadiazol-3-yl | CH₃ | CH₃ | |
| 2.171 | 4-Trifluoromethyl-1,2,5-thiadiazol-3-yl | CH₃ | CH₃ | |
| 2.172 | Thiazol-2-yl | CH₃ | CH₃ | |
| 2.173 | 4-Methylthiazol-2-yl | CH₃ | CH₃ | |
| 2.174 | 5-Methylthiazol-2-yl | CH₃ | CH₃ | |
| 2.175 | 4-Methylthiazol-5-yl | CH₃ | CH₃ | |
| 2.176 | 5-Methylthiazol-4-yl | CH₃ | CH₃ | |
| 2.177 | 2-Methylthiazol-4-yl | CH₃ | CH₃ | |
| 2.178 | 2-Methylthiazol-5-yl | CH₃ | CH₃ | |
| 2.179 | 4-Methoxythiazol-2-yl | CH₃ | CH₃ | |
| 2.180 | 5-Methoxythiazol-2-yl | CH₃ | CH₃ | |
| 2.181 | 4-Methoxythiazol-5-yl | CH₃ | CH₃ | |
| 2.182 | 5-Methoxythiazol-4-yl | CH₃ | CH₃ | |
| 2.183 | 2-Methoxythiazol-4-yl | CH₃ | CH₃ | |
| 2.184 | 2-Methoxythiazol-5-yl | CH₃ | CH₃ | |
| 2.185 | 4-Trifluoromethylthiazol-2-yl | CH₃ | CH₃ | |
| 2.186 | 5-Trifluoromethylthiazol-2-yl | CH₃ | CH₃ | |
| 2.187 | 4-Trifluoromethylthiazol-5-yl | CH₃ | CH₃ | |
| 2.188 | 5-Trifluoromethylthiazol-4-yl | CH₃ | CH₃ | |
| 2.189 | 2-Trifluoromethylthiazol-4-yl | CH₃ | CH₃ | |
| 2.190 | 2-Trifluoromethylthiazol-5-yl | CH₃ | CH₃ | |
| 2.191 | 4-Methylthiothiazol-2-yl | CH₃ | CH₃ | |
| 2.192 | 5-Methylthiothiazol-2-yl | CH₃ | CH₃ | |
| 2.193 | 4-Methylthiothiazol-5-yl | CH₃ | CH₃ | |
| 2.194 | 5-Methylthiothiazol-4-yl | CH₃ | CH₃ | |
| 2.195 | 2-Methylthiothiazol-4-yl | CH₃ | CH₃ | |
| 2.196 | 2-Methylthiothiazol-5-yl | CH₃ | CH₃ | |
| 2.197 | Isothiazol-3-yl | CH₃ | CH₃ | |
| 2.198 | Isothiazol-4-yl | CH₃ | CH₃ | |
| 2.199 | Isothiazol-5-yl | CH₃ | CH₃ | |
| 2.200 | 5-Methylisothiazol-3-yl | CH₃ | CH₃ | |
| 2.201 | 4-Methylisothiazol-3-yl | CH₃ | CH₃ | |
| 2.202 | 5-Methylisothiazol-4-yl | CH₃ | CH₃ | |
| 2.203 | 3-Methylisothiazol-4-yl | CH₃ | CH₃ | |
| 2.204 | 3-Methylisothiazol-5-yl | CH₃ | CH₃ | |
| 2.205 | 4-Methylisothiazol-5-yl | CH₃ | CH₃ | |
| 2.206 | 5-Methylthioisothiazol-3-yl | CH₃ | CH₃ | |
| 2.207 | 4-Methylthioisothiazol-3-yl | CH₃ | CH₃ | |
| 2.208 | 5-Methylthioisothiazol-4-yl | CH₃ | CH₃ | |
| 2.209 | 3-Methylthioisothiazol-4-yl | CH₃ | CH₃ | |
| 2.210 | 3-Methylthioisothiazol-5-yl | CH₃ | CH₃ | |
| 2.211 | 4-Methylthiaisothiazol-5-yl | CH₃ | CH₃ | |
| 2.212 | 5-Methoxyisothiazol-3-yl | CH₃ | CH₃ | |
| 2.213 | 4-Methoxyisothiazol-3-yl | CH₃ | CH₃ | |
| 2.214 | 5-Methoxyisothiazol-4-yl | CH₃ | CH₃ | |
| 2.215 | 3-Methoxyisothiazol-4-yl | CH₃ | CH₃ | |
| 2.216 | 3-Methoxyisothiazol-5-yl | CH₃ | CH₃ | |
| 2.217 | 4-Methoxyisothiazol-5-yl | CH₃ | CH₃ | |
| 2.218 | 5-Trifluoromethylisothiazol-3-yl | CH₃ | CH₃ | |
| 2.219 | 4-Trifluoromethylisothiazol-3-yl | CH₃ | CH₃ | |
| 2.220 | 5-Trifluoromethylisothiazol-4-yl | CH₃ | CH₃ | |
| 2.221 | 3-Trifluoromethylisothiazol-4-yl | CH₃ | CH₃ | |
| 2.222 | 3-Trifluoromethylisothiazol-5-yl | CH₃ | CH₃ | |
| 2.223 | 4-Trifluoromethylisothiazol-5-yl | CH₃ | CH₃ | |
| 2.224 | 4-Chloroisothiazol-5-yl | CH₃ | CH₃ | |
| 2.225 | 4-Fluoroisothiazol-5-yl | CH₃ | CH₃ | |
| 2.226 | 4-Fluoro-3-methylisothiazol-5-yl | CH₃ | CH₃ | |
| 2.227 | 1-Methylpyrrol-2-yl | CH₃ | CH₃ | |
| 2.228 | 1-Methylpyrrol-3-yl | CH₃ | CH₃ | |
| 2.229 | 1-Ethylpyrrol-2-yl | CH₃ | CH₃ | |
| 2.230 | 1-Ethylpyrrol-3-yl | CH₃ | CH₃ | |
| 2.231 | 1-Phenylpyrrol-2-yl | CH₃ | CH₃ | |
| 2.232 | 1-Phenylpyrrol-3-yl | CH₃ | CH₃ | |
| 2.233 | Pyrazol-3-yl | CH₃ | CH₃ | |
| 2.234 | Pyrazol-4-yl | CH₃ | CH₃ | |
| 2.235 | Pyrazol-5-yl | CH₃ | CH₃ | |
| 2.236 | 1-Methylpyrazol-3-yl | CH₃ | CH₃ | |
| 2.237 | 1-Methylpyrazol-4-yl | CH₃ | CH₃ | |
| 2.238 | 1-Methylpyrazol-5-yl | CH₃ | CH₃ | |
| 2.239 | 4-Methylpyrazol-3-yl | CH₃ | CH₃ | |
| 2.240 | 5-Methylpyrazol-3-yl | CH₃ | CH₃ | |
| 2.241 | 3-Methylpyrazol-4-yl | CH₃ | CH₃ | |
| 2.242 | 5-Methylpyrazol-4-yl | CH₃ | CH₃ | |
| 2.243 | 3-Methylpyrazol-5-yl | CH₃ | CH₃ | |
| 2.244 | 4-Methylpyrazol-5-yl | CH₃ | CH₃ | |
| 2.245 | 1,4-Dimethylpyrazol-3-yl | CH₃ | CH₃ | |
| 2.246 | 1,5-Dimethylpyrazol-3-yl | CH₃ | CH₃ | |
| 2.247 | 1,3-Dimethylpyrazol-4-yl | CH₃ | CH₃ | |
| 2.248 | 1,5-Dimethylpyrazol-4-yl | CH₃ | CH₃ | |
| 2.249 | 1,3-Dimethylpyrazol-5-yl | CH₃ | CH₃ | |
| 2.250 | 1,4-Dimethylpyrazol-5-yl | CH₃ | CH₃ | |
| 2.251 | 1-Phenylpyrazol-3-yl | CH₃ | CH₃ | |
| 2.252 | 1-Phenylpyrazol-4-yl | CH₃ | CH₃ | |
| 2.253 | 1-Phenylpyrazol-5-yl | CH₃ | CH₃ | |
| 2.254 | 4-Phenylpyrazol-3-yl | CH₃ | CH₃ | |
| 2.255 | 5-Phenylpyrazol-3-yl | CH₃ | CH₃ | |
| 2.256 | 3-Phenylpyrazol-4-yl | CH₃ | CH₃ | |
| 2.257 | 5-Phenylpyrazol-4-yl | CH₃ | CH₃ | |
| 2.258 | 3-Phenylpyrazol-5-yl | CH₃ | CH₃ | |
| 2.259 | 4-Phenylpyrazol-5-yl | CH₃ | CH₃ | |
| 2.260 | 1-Phenyl-4-methylpyrazol-3-yl | CH₃ | CH₃ | |
| 2.261 | 1-Phenyl-5-methylpyrazol-3-yl | CH₃ | CH₃ | |
| 2.262 | 1-Phenyl-3-methylpyrazol-4-yl | CH₃ | CH₃ | |
| 2.263 | 1-Phenyl-5-methylpyrazol-4-yl | CH₃ | CH₃ | |
| 2.264 | 1-Phenyl-3-methylpyrazol-5-yl | CH₃ | CH₃ | |
| 2.265 | 1-Phenyl-4-methylpyrazol-5-yl | CH₃ | CH₃ | |
| 2.266 | 1-Methoxypyrazol-3-yl | CH₃ | CH₃ | |
| 2.267 | 1-Methoxypyrazol-4-yl | CH₃ | CH₃ | |
| 2.268 | 1-Methoxypyrazol-5-yl | CH₃ | CH₃ | |
| 2.269 | 4-Fluoropyrazol-3-yl | CH₃ | CH₃ | |
| 2.270 | 5-Fluoropyrazol-3-yl | CH₃ | CH₃ | |
| 2.271 | 3-Fluoropyrazol-4-yl | CH₃ | CH₃ | |
| 2.272 | 5-Fluoropyrazol-4-yl | CH₃ | CH₃ | |
| 2.273 | 3-Fluoropyrazol-5-yl | CH₃ | CH₃ | |
| 2.274 | 4-Fluoropyrazol-5-yl | CH₃ | CH₃ | |
| 2.275 | 4-Fluoro-1-methylpyrazol-3-yl | CH₃ | CH₃ | |
| 2.276 | 5-Fluoro-1-methylpyrazol-3-yl | CH₃ | CH₃ | |
| 2.277 | 3-Fluoro-1-methylpyrazol-4-yl | CH₃ | CH₃ | |

TABLE 2-continued

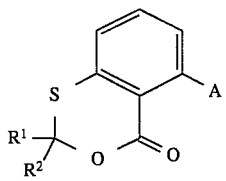

| No. | A | R¹ | R² | Physical data |
|---|---|---|---|---|
| 2.278 | 5-Fluoro-1-methylpyrazol-4-yl | CH₃ | CH₃ | |
| 2.279 | 3-Fluoro-1-methylpyrazol-5-yl | CH₃ | CH₃ | |
| 2.280 | 4-Fluoro-1-methylpyrazol-5-yl | CH₃ | CH₃ | |
| 2.281 | 4-Trifluoromethyl-1-methyl-pyrazol-3-yl | CH₃ | CH₃ | |
| 2.282 | 5-Trifluoromethyl-1-methyl-pyrazol-3-yl | CH₃ | CH₃ | |
| 2.283 | 3-Trifluoromethyl-1-methyl-pyrazol-4-yl | CH₃ | CH₃ | |
| 2.284 | 5-Trifluoromethyl-1-methyl-pyrazol-4-yl | CH₃ | CH₃ | |
| 2.285 | 3-Trifluoromethyl-1-methyl-pyrazol-5-yl | CH₃ | CH₃ | |
| 2.286 | 4-Trifluoromethyl-1-methyl-pyrazol-4-yl | CH₃ | CH₃ | |
| 2.287 | Imidazol-2-yl | CH₃ | CH₃ | |
| 2.288 | Imidazol-4-yl | CH₃ | CH₃ | |
| 2.289 | 1-Methylimidazol-2-yl | CH₃ | CH₃ | |
| 2.290 | 1-Methylimidazol-4-yl | CH₃ | CH₃ | |
| 2.291 | 1-Methylimidazol-5-yl | CH₃ | CH₃ | |
| 2.292 | 4-Methylimidazol-2-yl | CH₃ | CH₃ | |
| 2.293 | 2-Methylimidazol-4-yl | CH₃ | CH₃ | |
| 2.294 | 5-Methylimidazol-4-yl | CH₃ | CH₃ | |
| 2.295 | 4-Methylimidazol-5-yl | CH₃ | CH₃ | |
| 2.296 | 1,4-Dimethylimidazol-2-yl | CH₃ | CH₃ | |
| 2.297 | 1,5-Dimethylimidazol-2-yl | CH₃ | CH₃ | |
| 2.298 | 1,2-Dimethylimidazol-4-yl | CH₃ | CH₃ | |
| 2.299 | 1,5-Dimethylimidazol-4-yl | CH₃ | CH₃ | |
| 2.300 | 1,2-Dimethylimidazol-5-yl | CH₃ | CH₃ | |
| 2.301 | 1,4-Dimethylimidazol-5-yl | CH₃ | CH₃ | |
| 2.302 | 1-Phenylimidazol-2-yl | CH₃ | CH₃ | |
| 2.303 | 1-Phenylimidazol-4-yl | CH₃ | CH₃ | |
| 2.304 | 1-Phenylimidazol-5-yl | CH₃ | CH₃ | |
| 2.305 | 1,2,3-Triazol-4-yl | CH₃ | CH₃ | |
| 2.306 | 1,2,4-Triazol-3-yl | CH₃ | CH₃ | |
| 2.307 | 1-Methyl-1,2,3-triazol-4-yl | CH₃ | CH₃ | |
| 2.308 | 1-Methyl-1,2,3-triazol-5-yl | CH₃ | CH₃ | |
| 2.307 | 2-Methyl-1,2,3-triazol-4-yl | CH₃ | CH₃ | |
| 2.308 | 2,4-Dimethyl-1,2,3-triazol-5-yl | CH₃ | CH₃ | |
| 2.309 | 1,4-Dimethyl-1,2,3-triazol-5-yl | CH₃ | CH₃ | |
| 2.310 | 1,5-Dimethyl-1,2,3-triazol-4-yl | CH₃ | CH₃ | |
| 2.311 | 1-Methyl-1,2,4-triazol-3-yl | CH₃ | CH₃ | |
| 2.312 | 1-Methyl-1,2,4-triazol-5-yl | CH₃ | CH₃ | |
| 2.313 | 4-Methyl-1,2,4-triazol-3-yl | CH₃ | CH₃ | |
| 2.314 | 1,3-Dimethyl-1,2,4-triazol-5-yl | CH₃ | CH₃ | |
| 2.315 | 1,5-Dimethyl-1,2,4-triazol-3-yl | CH₃ | CH₃ | |
| 2.316 | 3,4-Dimethyl-1,2,4-triazol-5-yl | CH₃ | CH₃ | |
| 2.317 | 1-Trifluoromethyl-1,2,4-triazol-3-yol | CH₃ | CH₃ | |
| 2.318 | 1-Trifluoromethyl-1,2,4-triazol-5-yl | CH₃ | CH₃ | |
| 2.319 | 4-Trifluoromethyl-1,2,4-triazol-3-yl | CH₃ | CH₃ | |
| 2.320 | Tetrazol-5-yl | CH₃ | CH₃ | |
| 2.321 | 2-Methylpyridin-4-yl | CH₃ | CH₃ | |
| 2.322 | 3-Methylpyridin-4-yl | CH₃ | CH₃ | |
| 2.323 | 2,3-Dimethylpyridin-4-yl | CH₃ | CH₃ | |
| 2.324 | 2,6-Dimethylpyridin-4-yl | CH₃ | CH₃ | |
| 2.325 | 2,5-Dimethylpyridin-4-yl | CH₃ | CH₃ | |
| 2.326 | 3,5-Dimethylpyridin-4-yl | CH₃ | CH₃ | |
| 2.327 | 2-Methoxypyridin-4-yl | CH₃ | CH₃ | |
| 2.328 | 3-Methoxypyridin-4-yl | CH₃ | CH₃ | |
| 2.329 | 2-Ethoxypyridin-4-yl | CH₃ | CH₃ | |
| 2.330 | 3-Ethoxypyridin-4-yl | CH₃ | CH₃ | |
| 2.331 | 2-Propoxypyridin-4-yl | CH₃ | CH₃ | |
| 2.332 | 3-Propoxypyridin-4-yl | CH₃ | CH₃ | |
| 2.333 | 2-Isopropoxypyridin-4-yl | CH₃ | CH₃ | |
| 2.334 | 3-Isopropoxypyridin-4-yl | CH₃ | CH₃ | |
| 2.335 | 2-(2,2,2-Trifluoroethoxy)-pyridin-4-yl | CH₃ | CH₃ | |
| 2.336 | 3-(2,2,2-Trifluoroethoxy)-pyridin-4-yl | CH₃ | CH₃ | |
| 2.337 | 2-Methylthiopyridin-4-yl | CH₃ | CH₃ | |
| 2.338 | 3-Methylthiopyridin-4-yl | CH₃ | CH₃ | |
| 2.339 | 2-Trifluoromethylpyridin-4-yl | CH₃ | CH₃ | |
| 2.340 | 3-Trifluoromethylpyridin-4-yl | CH₃ | CH₃ | |
| 2.341 | 2-Fluoropyridin-4-yl | CH₃ | CH₃ | |
| 2.342 | 3-Fluoropyridin-4-yl | CH₃ | CH₃ | |
| 2.343 | 1-Methyl-5-methylthio-1,2,4-triazol-3-yl | CH₃ | CH₃ | |
| 2.344 | 2-Trifluoromethoxypyridin-4-yl | CH₃ | CH₃ | |
| 2.345 | 3-Trifluoromethoxypyridin-4-yl | CH₃ | CH₃ | |
| 2.346 | 2-(2,2,2-Trifluoroethoxy)-pyridin-5-yl | CH₃ | CH₃ | |
| 2.347 | 2-Dimethylaminoxypyridin-5-yl | CH₃ | CH₃ | |
| 2.348 | 2-Cyclopentyloxypyridin-5-yl | CH₃ | CH₃ | |
| 2.349 | 2-Methylpyridin-3-yl | CH₃ | CH₃ | |
| 2.350 | 4-Methylpyridin-3-yl | CH₃ | CH₃ | |
| 2.351 | 3-Methylpyridin-5-yl | CH₃ | CH₃ | |
| 2.352 | 2-Methylpyridin-5-yl | CH₃ | CH₃ | |
| 2.353 | 2,4-Dimethylpyridin-3-yl | CH₃ | CH₃ | |
| 2.354 | 2,6-Dimethylpyridin-3-yl | CH₃ | CH₃ | |
| 2.355 | 2,3-Dimethylpyridin-5-yl | CH₃ | CH₃ | |
| 2.356 | 2,4-Dimethylpyridin-5-yl | CH₃ | CH₃ | |
| 2.357 | 2-Methoxypyridin-3-yl | CH₃ | CH₃ | |
| 2.358 | 4-Methoxypyridin-3-yl | CH₃ | CH₃ | |
| 2.359 | 3-Methoxypyridin-5-yl | CH₃ | CH₃ | |
| 2.360 | 2-Ethoxypyridin-3-yl | CH₃ | CH₃ | |
| 2.361 | 4-Ethoxypyridin-3-yl | CH₃ | CH₃ | |
| 2.362 | 3-Ethoxypyridin-5-yl | CH₃ | CH₃ | |
| 2.363 | 2-Propoxypyridin-3-yl | CH₃ | CH₃ | |
| 2.364 | 4-Propoxypyridin-3-yl | CH₃ | CH₃ | |
| 2.365 | 3-Propoxypyridin-5-yl | CH₃ | CH₃ | |
| 2.366 | 2-Propoxypyridin-5-yl | CH₃ | CH₃ | |
| 2.367 | 2-Isopropoxypyridin-3-yl | CH₃ | CH₃ | |
| 2.368 | 4-Isopropoxypyridin-3-yl | CH₃ | CH₃ | |
| 2.369 | 3-Isopropoxypyridin-5-yl | CH₃ | CH₃ | |
| 2.370 | 2-Methylthiopyridin-3-yl | CH₃ | CH₃ | |
| 2.371 | 4-Methylthiopyridin-3-yl | CH₃ | CH₃ | |
| 2.372 | 3-Methylthiopyridin-5-yl | CH₃ | CH₃ | |
| 2.373 | 2-(2,2,2-Trifluoroethoxy)-pyridin-3-yl | CH₃ | CH₃ | |
| 2.374 | 4-(2,2,2-Trifluoroethoxy)-pyridin-3-yl | CH₃ | CH₃ | |
| 2.375 | 3-(2,2,2-Trifluoroethoxy)-pyridin-5-yl | CH₃ | CH₃ | |
| 2.376 | 2-(2,2,2-Trifluoroethoxy)-pyridin-5-yl | CH₃ | CH₃ | |
| 2.377 | 2-Trifluoromethylpyridin-3-yl | CH₃ | CH₃ | |
| 2.378 | 4-Trifluoromethylpyridin-3-yl | CH₃ | CH₃ | |
| 2.379 | 3-Trifluoromethylpyridin-5-yl | CH₃ | CH₃ | |
| 2.380 | 2-Trifluoromethylpyridin-5-yl | CH₃ | CH₃ | |
| 2.381 | 2-Fluoropyridin-3-yl | CH₃ | CH₃ | |
| 2.382 | 4-Fluoropyridin-3-yl | CH₃ | CH₃ | |
| 2.383 | 3-Fluoropyridin-5-yl | CH₃ | CH₃ | |
| 2.384 | 2-Fluoropyridin-5-yl | CH₃ | CH₃ | |
| 2.385 | 2-Trifluoromethoxypyridin-3-yl | CH₃ | CH₃ | |
| 2.386 | 4-Trifluoromethoxypyridin-3-yl | CH₃ | CH₃ | |
| 2.387 | 3-Trifluoromethoxypyridin-5-yl | CH₃ | CH₃ | |
| 2.388 | 2-Trifluoromethoxypyridin-5-yl | CH₃ | CH₃ | |
| 2.389 | 3-(2,2,2-Trifluoroethoxy)-pyridin-5-yl | CH₃ | CH₃ | |
| 2.390 | 3-Dimethylaminoxypyridin-5-yl | CH₃ | CH₃ | |
| 2.391 | 2-(2,2,2-Trifluoroethoxy)- | CH₃ | CH₃ | |

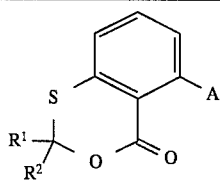

TABLE 2-continued

[Structure: benzoate with S-C(R¹)(R²)-O group and A substituent]

| No. | A | R¹ | R² | Physical data |
|---|---|---|---|---|
| | pyridin-3-yl | | | |
| 2.392 | 2-Dimethylaminoxypyridin-3-yl | CH₃ | CH₃ | |
| 2.393 | 4-(2,2,2-Trifluoroethoxy)-pyridin-3-yl | CH₃ | CH₃ | |
| 2.394 | 4-Dimethylaminoxypyridin-3-yl | CH₃ | CH₃ | |
| 2.395 | 3-(2,2,2-Trifluoroethoxy)-pyridin-2-yl | CH₃ | CH₃ | |
| 2.396 | 4-(2,2,2-Trifluoroethoxy)-pyridin-2-yl | CH₃ | CH₃ | |
| 2.397 | 5-(2,2,2-Trifluoroethoxy)-pyridin-2-yl | CH₃ | CH₃ | |
| 2.398 | 6-(2,2,2-Trifluoroethoxy)-pyridin-2-yl | CH₃ | CH₃ | |
| 2.399 | 6-Cyclopentyloxypyridin-2-yl | CH₃ | CH₃ | |
| 2.400 | 3-Methylpyridin-2-yl | CH₃ | CH₃ | |
| 2.401 | 4-Methylpyridin-2-yl | CH₃ | CH₃ | |
| 2.402 | 3,4-Dimethylpyridin-2-yl | CH₃ | CH₃ | |
| 2.403 | 3,5-Dimethylpyridin-2-yl | CH₃ | CH₃ | |
| 2.404 | 3,6-Dimethylpyridin-2-yl | CH₃ | CH₃ | |
| 2.405 | 4,5-Dimethylpyridin-2-yl | CH₃ | CH₃ | |
| 2.406 | 5,6-Dimethylpyridin-2-yl | CH₃ | CH₃ | |
| 2.407 | 3-Methoxypyridin-2-yl | CH₃ | CH₃ | |
| 2.408 | 4-Methoxypyridin-2-yl | CH₃ | CH₃ | |
| 2.409 | 5-Methoxypyridin-2-yl | CH₃ | CH₃ | |
| 2.410 | 3-Ethoxypyridin-2-yl | CH₃ | CH₃ | |
| 2.411 | 4-Ethoxypyridin-2-yl | CH₃ | CH₃ | |
| 2.412 | 5-Ethoxypyridin-2-yl | CH₃ | CH₃ | |
| 2.413 | 3-Propoxypyridin-2-yl | CH₃ | CH₃ | |
| 2.414 | 4-Propoxypyridin-2-yl | CH₃ | CH₃ | |
| 2.415 | 5-Propoxypyridin-2-yl | CH₃ | CH₃ | |
| 2.416 | 6-Propoxypyridin-2-yl | CH₃ | CH₃ | |
| 2.417 | 3-Isopropoxypyridin-2-yl | CH₃ | CH₃ | |
| 2.418 | 4-Isopropoxypyridin-2-yl | CH₃ | CH₃ | |
| 2.419 | 5-Isopropoxypyridin-2-yl | CH₃ | CH₃ | |
| 2.420 | 3-Methylthiopyridin-2-yl | CH₃ | CH₃ | |
| 2.421 | 4-Methylthiopyridin-2-yl | CH₃ | CH₃ | |
| 2.422 | 5-Methylthiopyridin-2-yl | CH₃ | CH₃ | |
| 2.423 | 3-Ethylthiopyridin-2-yl | CH₃ | CH₃ | |
| 2.424 | 4-Ethylthiopyridin-2-yl | CH₃ | CH₃ | |
| 2.425 | 5-Ethylthiopyridin-2-yl | CH₃ | CH₃ | |
| 2.426 | 6-Ethylthiopyridin-2-yl | CH₃ | CH₃ | |
| 2.427 | 3-Trifluoromethylpyridin-2-yl | CH₃ | CH₃ | |
| 2.428 | 4-Trifluoromethylpyridin-2-yl | CH₃ | CH₃ | |
| 2.429 | 5-Trifluoromethylpyridin-2-yl | CH₃ | CH₃ | |
| 2.430 | 6-Trifluoromethylpyridin-2-yl | CH₃ | CH₃ | |
| 2.431 | 3-Fluoropyridin-2-yl | CH₃ | CH₃ | |
| 2.432 | 4-Fluoropyridin-2-yl | CH₃ | CH₃ | |
| 2.433 | 5-Fluoropyridin-2-yl | CH₃ | CH₃ | |
| 2.434 | 6-Fluoropyridin-2-yl | CH₃ | CH₃ | |
| 2.435 | 3-Trifluoromethoxypyridin-2-yl | CH₃ | CH₃ | |
| 2.436 | 4-Trifluoromethoxypyridin-2-yl | CH₃ | CH₃ | |
| 2.437 | 5-Trifluoromethoxypyridin-2-yl | CH₃ | CH₃ | |
| 2.438 | 6-Trifluoromethoxypyridin-2-yl | CH₃ | CH₃ | |
| 2.439 | 4-Dimethylaminoxypyridin-2-yl | CH₃ | CH₃ | |
| 2.440 | 3-Dimethylaminoxypyridin-2-yl | CH₃ | CH₃ | |
| 2.441 | 5-Dimethylaminoxypyridin-2-yl | CH₃ | CH₃ | |
| 2.442 | 6-Dimethylaminoxypyridin-2-yl | CH₃ | CH₃ | |
| 2.443 | Pyrimidin-2-yl | CH₃ | CH₃ | |
| 2.444 | Pyrimidin-4-yl | CH₃ | CH₃ | |
| 2.445 | Pyrimidin-5-yl | CH₃ | CH₃ | |
| 2.446 | 4-Methoxypyrimidin-2-yl | CH₃ | CH₃ | |
| 2.447 | 5-Methoxypyrimidin-2-yl | CH₃ | CH₃ | |
| 2.448 | 4,6-Dimethoxypyrimidin-2-yl | CH₃ | CH₃ | |
| 2.449 | 2-Methoxypyrimidin-4-yl | CH₃ | CH₃ | |
| 2.450 | 6-Methoxypyrimidin-4-yl | CH₃ | CH₃ | |
| 2.451 | 2,6-Dimethoxypyrimidin-4-yl | CH₃ | CH₃ | |
| 2.452 | 2-Methoxypyrimidin-5-yl | CH₃ | CH₃ | |
| 2.453 | 4-Methoxypyrimidin-5-yl | CH₃ | CH₃ | |
| 2.454 | 2,4-Dimethoxypyrimidin-5-yl | CH₃ | CH₃ | |
| 2.455 | 4-Methylthiopyrimidin-2-yl | CH₃ | CH₃ | |
| 2.456 | 2-(2,2,2-Trifluoroethoxy)-pyrimidin-4-yl | CH₃ | CH₃ | |
| 2.457 | 2-(2-Dimethylaminoethoxy)-pyridin-5-yl | CH₃ | CH₃ | |
| 2.458 | 2-(2-Methoxyethoxy)-pyridin-5-yl | CH₃ | CH₃ | |
| 2.459 | 6-(2-Methoxyethyl)-pyridin-2-yl | CH₃ | CH₃ | |
| 2.460 | 2-(Methoxymethoxy)-pyridin-5-yl | CH₃ | CH₃ | |
| 2.461 | 6-(Methoxymethoxy)-pyridin-2-yl | CH₃ | CH₃ | |
| 2.462 | 2-(Methoxymethyl)-pyridin-5-yl | CH₃ | CH₃ | |
| 2.463 | 6-(Methoxymethyl)-pyridin-2-yl | CH₃ | CH₃ | |
| 2.464 | 6-(Methylthiomethyl)-pyridin-2-yl | CH₃ | CH₃ | |
| 2.465 | 1-Naphthyl | CH₃ | CH₃ | |
| 2.466 | 2-Naphthyl | CH₃ | CH₃ | |
| 2.467 | 5-Benzotriazolyl | CH₃ | CH₃ | |
| 2.468 | 2-Benzothiazolyl | CH₃ | CH₃ | |
| 2.469 | 2-Benzoxazolyl | CH₃ | CH₃ | |
| 2.470 | Quinolin-2-yl | CH₃ | CH₃ | |
| 2.471 | Quinolin-4-yl | CH₃ | CH₃ | |
| 2.472 | Benzothien-2-yl | CH₃ | CH₃ | |
| 2.473 | 2,3-Dihydrofuran-4-yl | CH₃ | CH₃ | |
| 2.474 | 1-Cyclopentadienyl | CH₃ | CH₃ | |
| 2.475 | 5-Cyclopentadienyl | CH₃ | CH₃ | |
| 2.476 | Vinyl | CH₃ | CH₃ | |
| 2.477 | 1-Chlorovinyl | CH₃ | CH₃ | |
| 2.478 | 2-Chlorovinyl | CH₃ | CH₃ | |
| 2.479 | 2-Propenyl | CH₃ | CH₃ | |
| 2.480 | 1-Propenyl | CH₃ | CH₃ | |
| 2.481 | 2-Methylpropen-1-yl | CH₃ | CH₃ | |
| 2.482 | 1-Propynyl | CH₃ | CH₃ | |
| 2.483 | Tetrahydropyran-4-yl | CH₃ | CH₃ | |
| 2.484 | Tetrahydropyran-3-yl | CH₃ | CH₃ | |
| 2.485 | Tetrahydrothiopyran-3-yl | CH₃ | CH₃ | |
| 2.486 | Tetrahydrothiopyran-4-yl | CH₃ | CH₃ | |
| 2.487 | N-Methylpiperidin-4-yl | CH₃ | CH₃ | |
| 2.488 | N-Methylpyrrolidin-2-yl | CH₃ | CH₃ | |
| 2.489 | Tetrahydrofuran-2-yl | CH₃ | CH₃ | |
| 2.490 | Tetrahydrofuran-3-yl | CH₃ | CH₃ | |
| 2.491 | 2-Allyloxypyridin-5-yl | CH₃ | CH₃ | |
| 2.492 | 6-Allyloxypyridin-2-yl | CH₃ | CH₃ | |
| 2.493 | 2-Methoxyphenyl | CH₃ | CH₃ | |
| 2.494 | 3-Methoxyphenyl | CH₃ | CH₃ | |
| 2.495 | 4-Methoxyphenyl | CH₃ | CH₃ | |
| 2.496 | 2-Ethoxyphenyl | CH₃ | CH₃ | |
| 2.497 | 3-Ethoxyphenyl | CH₃ | CH₃ | |
| 2.498 | 4-Ethoxyphenyl | CH₃ | CH₃ | |
| 2.499 | 2-Propoxyphenyl | CH₃ | CH₃ | |
| 2.500 | 3-Propoxyphenyl | CH₃ | CH₃ | |
| 2.501 | 4-Propoxyphenyl | CH₃ | CH₃ | |
| 2.502 | 2-Isopropyloxyphenyl | CH₃ | CH₃ | |
| 2.503 | 3-Isopropyloxyphenyl | CH₃ | CH₃ | |
| 2.504 | 4-Isopropyloxyphenyl | CH₃ | CH₃ | |
| 2.505 | 4-(2,2,2-Trifluoroethoxy)phenyl | CH₃ | CH₃ | |
| 2.506 | 3-(2,2,2-Trifluoroethoxy)phenyl | CH₃ | CH₃ | |
| 2.507 | 2-(2,2,2-Trifluoroethoxy)phenyl | CH₃ | CH₃ | |
| 2.508 | 4-Cyclopropyloxyphenyl | CH₃ | CH₃ | |
| 2.509 | 4-(Trifluoromethoxy)phanyl | CH₃ | CH₃ | |
| 2.510 | 4-(Difluoromethoxy)phenyl | CH₃ | CH₃ | |
| 2.511 | 4-(Difluorochloromethoxy)phenyl | CH₃ | CH₃ | |

TABLE 2-continued

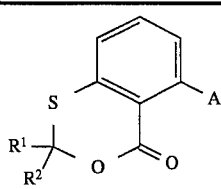

| No. | A | R¹ | R² | Physical data |
|---|---|---|---|---|
| 2.512 | 4-(Methoxymethoxy)phenyl | CH₃ | CH₃ | |
| 2.513 | 4-(2-Methoxyethoxy)phenyl | CH₃ | CH₃ | |
| 2.514 | 4-(Ethoxymethoxy)phenyl | CH₃ | CH₃ | |
| 2.515 | 4-(Ethoxymethyl)phenyl | CH₃ | CH₃ | |
| 2.516 | 4-(Methylthio)phenyl | CH₃ | CH₃ | |
| 2.517 | 4-(Methylthiomethyl)phenyl | CH₃ | CH₃ | |
| 2.518 | 4-(2-Dimethylamino-ethoxy)phenyl | CH₃ | CH₃ | |
| 2.519 | 4-(2-Propenyl)phenyl | CH₃ | CH₃ | |
| 2.520 | 4-(Vinyloxy)phenyl | CH₃ | CH₃ | |
| 2.521 | 4-(Allyloxy)phenyl | CH₃ | CH₃ | |
| 2.522 | 4-Fluorophenyl | CH₃ | CH₃ | |
| 2.523 | Cyclopenten-3-yl | CH₃ | CH₃ | |
| 2.524 | Cyclopenten-1-yl | CH₃ | CH₃ | |
| 2.525 | Cyclohexen-1-yl | CH₃ | CH₃ | |
| 2.526 | Cyclohexen-3-yl | CH₃ | CH₃ | |
| 2.527 | Fluorosulfonyloxy | CH₃ | CH₃ | |
| 2.528 | Chlorine | CH₃ | CH₃ | |
| 2.529 | Iodine | CH₃ | CH₃ | |
| 2.530 | Fluorine | CH₃ | CH₃ | |
| 2.531 | Cyano | CH₃ | CH₃ | |
| 2.532 | Nitro | CH₃ | CH₃ | |
| 2.533 | Formyl | CH₃ | CH₃ | |
| 2.534 | 6-Dimethylaminopyridin-2-yl | CH₃ | CH₃ | |
| 2.535 | 2-Dimethylaminopyridin-5-yl | CH₃ | CH₃ | |
| 2.536 | 4-Dimethylaminophenyl | CH₃ | CH₃ | |
| 2.537 | 2-Dimethylaminopyridin-3-yl | CH₃ | CH₃ | |
| 2.538 | 2-(2-Propaniminoxy)pyridin-5-yl | CH₃ | CH₃ | |
| 2.539 | 6-(2-Propaniminoxy)pyridin-2-yl | CH₃ | CH₃ | |
| 2.540 | 2-(2-Propaniminoxy)pyridin-3-yl | CH₃ | CH₃ | |
| 2.541 | Ethyl | CH₃ | CH₃ | |
| 2.542 | Propyl | CH₃ | CH₃ | |
| 2.543 | Methoxymethyl | CH₃ | CH₃ | |
| 2.544 | 2-Methoxyethyl | CH₃ | CH₃ | |
| 2.545 | 1-Chloroethyl | CH₃ | CH₃ | |
| 2.546 | 2,2,2-Trifluoroethyl | CH₃ | CH₃ | |
| 2.547 | Methylthiomethyl | CH₃ | CH₃ | |
| 2.548 | 3-(2-Propaniminoxy)propenyl | CH₃ | CH₃ | |
| 2.549 | (2-Propaniminoxy)methyl | CH₃ | CH₃ | |

δ (C): ¹H-NMR in CDCl₃, data in [ppm]
δ (D): ¹H-NMR in [D₆]-dimethyl sulfoxide, data in [ppm]

The compounds I or the herbicidal compositions containing them and their environmentally tolerable salts of, for example, alkali metals, alkaline earth metals or ammonia and amines or the herbicidal compositions containing them can control broad-leaved weeds and grass weeds very well in crops such as wheat, rice, maize, soybeans and cotton without noticeably damaging the crop plants. This effect occurs especially at low application rates.

Taking into account the variety of application methods, the compounds I or compositions containing them can additionally be employed in a further range of crop plants for the elimination of undesired plants. The following crops, for example, are suitable: Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N. rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.

Moreover, the compounds I can also be employed in crops which have been made largely resistant to the action of I or other herbicides by breeding and/or by means of genetic engineering methods.

The application of the herbicidal compositions or of the active compounds can be carried out pre-emergence or post-emergence. If the active compounds are less tolerable for certain crop plants, application techniques can be used in which the herbicidal compositions are sprayed with the aid of spray equipment such that the leaves of the sensitive crop plants are not affected if possible, while the active compounds reach the leaves of undesired plants growing under them or the uncovered soil surface (post-directed, lay-by).

The compounds I or the herbicidal compositions containing them can be applied by spraying, atomizing, dusting, broadcasting or watering for example in the form of directly sprayable aqueous solutions, powders, suspensions, alternatively high-percentage aqueous, oily or other suspensions or dispersions, emulsions, oil dispersions, pastes, dusting compositions, broadcasting compositions or granules. The application forms depend on the intended use; in each case, if possible, they should guarantee the finest dispersion of the active compounds according to the invention.

Suitable inert auxiliaries for the preparation of directly sprayable solutions, emulsions, pastes or oil dispersions are essentially: mineral oil fractions of medium to high boiling point such as kerosene or diesel oil, additionally coal tar oils and oils of vegetable or animal origin, aliphatic, cyclic and aromatic hydrocarbons, eg. paraffins, tetrahydronaphthalene, alkylated naphthalenes or their derivatives, alkylated benzenes and their derivatives, alcohols such as methanol, ethanol, propanol, butanol and cyclohexanol, ketones such as cyclohexanone, or strongly polar solvents, eg. amines such as N-methylpyrrolidone, or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant and possibly solvent or oil can also be prepared, which are suitable for dilution with water.

Suitable surface-active substances are the alkali metal, alkaline earth metal or ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules, can be prepared by binding the active substances to solid carriers. Solid carriers are mineral earths such as silica gel, silicic acids, silicates, talc, kaolin, limestone, lime, chalk, bole, loses, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal meal, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (according to NMR spectrum). The compounds I according to the invention can be formulated, for example, as follows:

I. 20 parts by weight of the compound No. I are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. I are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. I are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. I are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. I are mixed with 97 parts by weight of finely divided kaolin. In this way, a dusting composition is obtained which contains 3% by weight of the active compound.

VI. 20 parts by weight of the active compound No. I are intimately mixed with 2 parts by weight of the calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

To widen the spectrum of action and to achieve synergistic effects, the cyclic acetals I can be mixed with numerous representatives of other herbicidal or growth-regulating active compound groups and applied together. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane- 1,3-dione derivatives which in the 2-position carry eg. a carboxyl or carbimino group, quinolinecarboxylic acid derivatives, imidazolinones, sulfonamides, sulfonylureas, aryloxy- or heteroaryloxyphenoxypropionic acids and their salts, esters and amides and others.

Additionally, it may be useful to apply the compounds I on their own or together in combination with other herbicides also additionally mixed with further crop protection agents, for example with agents for the control of pests or phytopathogenic fungi or bacteria. Of interest is also the miscibility with mineral salt solutions, which are employed for the elimination of nutritional and trace element deficiencies. Nonphytotoxic oils and oil concentrates can also be added.

Depending on the target of control, time of year, target plants and stage of growth, the application rates of active compound are from 0.001 to 3.0 kg/ha of active substance (a.s.).

Use examples

It was possible to show the herbicidal action of the cyclic acetals of the formula I by greenhouse tests:

The cultivation containers used were plastic flowerpots containing loamy sand containing about 3.0% humus as a substrate. The seeds of the test plants were sown separately according to species.

In the case of pre-emergence treatment, the active compounds, suspended in water or emulsified, were applied directly after sowing by means of finely dispersing nozzles. The containers were lightly watered in order to promote germination and growth, and then covered with transparent plastic hoods until the plants had taken root. This covering causes uniform germination of the test plants if this has not been adversely affected by the active compounds.

For the purpose of post-emergence treatment, the test plants were first raised, depending on growth form, to a growth height of from 3 to 15 cm and only then treated with the active compounds suspended in water or emulsified. For this, the test plants were either sown directly and raised in the same containers or they are first raised separately as seed plants and transplanted into the test containers a few days before the treatment. The application rate for post-emergence treatment was 3.0 kg/ha of a.s.

The plants were kept in a species-specific manner at 10°–25° C. or 20°–35° C. The test period extended over a period of from 2 to 4 weeks. During this time, the plants were tended, and their reaction to the individual treatments was assessed.

Assessment was carried out on a scale of from 0 to 100. 100 here means no emergence of the plants or complete destruction of at least the above-ground parts and 0 means no damage or a normal course of growth.

We claim:

1. A method for controlling undesired plant growth, which comprises applying a herbicidally active amount of a cyclic acetal of the formula I

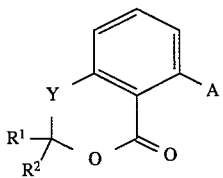

where the substituents have the following meanings:

$R^1$ and $R^2$ are hydrogen;

$C_1$–$C_4$-alkyl, this radical in each case being able to carry one to five halogen atoms and/or one to two $C_1$–$C_4$-alkoxy groups;

phenyl, this radical in each case being able to carry one to five halogen atoms and/or one to two of the following groups: $C_1$–$C_4$-alkyl, $C_1$–$C_4$-alkoxy, $C_1$–$C_4$-haloalkyl or nitro;

in addition the two radicals together can be a $C_2$–$C_6$-alkylene chain which can be substituted by one to five halogen atoms and/or $C_1$–$C_4$-alkyl radicals;

Y is oxygen or sulfur;

A is a radical $A^1$ to $A^6$;

$A^1$ is hydroxyl;

$A^2$ is a halogen atom, $C_1$–$C_4$-haloalkylsulfonyloxy, $C_1$–$C_4$-alkylsulfonyloxy or fluorosulfonyloxy;

$A^3$ is cyano, nitro or formyl;

$A^4$ is a phenyl ring or a 5- or 6-membered saturated or unsaturated heterocycle having up to four heteroatoms from the group consisting of nitrogen, sulfur and oxygen in the ring, each of which can be substituted by up to five radicals $R^{31}$ to $R^{35}$;

naphthyl or a benzo-fused 5- or 6-membered heteroaromatic having 1 to 3 heteroatoms from the group consisting of nitrogen, sulfur and oxygen in the ring, which can be substituted by up to five radicals $R^{31}$ to $R^{35}$;

$A^5$ is a $C_2$–$C_6$-alkenyl, $C_3$–$C_8$-cycloalkenyl, $C_5$–$C_8$-cycloalkadienyl or $C_2$–$C_6$-alkynyl group, each of which can carry up to seven substituents $R^{31}$ to $R^{37}$;

$A^6$ is a $C_1$–$C_8$-alkyl or $C_3$–$C_8$-cycloalkyl group, each of which can carry up to seven substituents $R^{31}$ to $R^{37}$;

$R^{31}$, $R^{32}$, $R^{33}$, $R^{34}$, $R^{35}$, $R^{36}$ and $R^{37}$ are a) a $C_3$–$C_8$-cycloalkyl group which can carry one to three $C_1$–$C_4$-alkyl radicals;

b) a $C_1$–$C_8$-alkyl group which can carry one to five halogen atoms and/or one of the following radicals: $C_1$–$C_4$-alkoxy, $C_1$–$C_4$-haloalkoxy, $C_1$–$C_4$-alkylthio, cyano, $C_3$–$C_8$-cycloalky or di-$C_1$–$C_4$-alkylamino;

c) a $C_1$–$C_8$-alkoxy group or a $C_3$–$C_5$-cycloalkoxy group, each of which can carry one to five halogen atoms and/or one of the following radicals: $C_1$–$C_4$-alkoxy, $C_1$–$C_4$-haloalkoxy, $C_1$–$C_4$-alkylthio, $C_3$–$C_8$-cycloalkyl or di-$C_1$–$C_4$-alkylamino;

d) a $C_1$–$C_4$-alkylthio group which can carry one to five halogen atoms and/or one of the following radicals: $C_1$–$C_4$-alkoxy, $C_1$–$C_4$-haloalkoxy, $C_1$–$C_4$-alkylthio, $C_3$–$C_8$-cycloalkyl or di-$C_1$–$C_4$-alkylamino;

e) a di-$C_1$–$C_4$-alkylamino or di-$C_1$–$C_4$-alkylaminoxy group, a $C_5$–$C_8$-cycloalkaniminoxy group or a $C_1$–$C_{10}$-alkaniminoxy group;

f) a $C_2$–$C_6$-alkenyl or a $C_2$–$C_6$-alkynyl group, which can carry one to five halogen atoms and/or one of the following radicals: $C_1$–$C_4$-alkoxy, $C_1$–$C_4$-haloalkoxy or $C_1$–$C_4$-alkylthio;

g) hydrogen;

h) nitro, halogen, cyano or tri-$C_1$–$C_4$-alkylsilyl to the plants or to their habitat.

* * * * *

UNITED STATES PATENT AND TRADEMARK OFFICE
CERTIFICATE OF CORRECTION

PATENT NO.: 5,569,640

DATED: October 29, 1996

INVENTOR(S): RHEINHEIMER et al.

It is certified that error appears in the above-identified patent and that said Letters Patent is hereby corrected as shown below:

On the cover page, insert the following information:

--[73] Assignee: BASF Aktiengesellschaft
Ludwigshafen, Germany--;

after the Primary Examiner, insert:

--Attorney, Agent, or Firm)Keil & Weinkauf--.

Signed and Sealed this

Twentieth Day of May, 1997

Attest:

BRUCE LEHMAN

Attesting Officer

Commissioner of Patents and Trademarks